United States Patent
Lehtonen et al.

(10) Patent No.: US 11,969,519 B1
(45) Date of Patent: Apr. 30, 2024

(54) IMPLANT COMPRISING MAGNESIUM ALLOY AND A METHOD FOR PREPARING THEREOF

(71) Applicant: Bioretec Oy, Tampere (FI)

(72) Inventors: Timo Lehtonen, Raisio (FI); Kimmo Lähteenkorva, Tampere (FI); Anna-Maija Haltia, Turenki (FI); Christopher Stahle, Tampere (FI)

(73) Assignee: Bioretec Oy, Tampere (FI)

( * ) Notice: Subject to any disclaimer, the term of this patent is extended or adjusted under 35 U.S.C. 154(b) by 0 days.

(21) Appl. No.: 18/324,388

(22) Filed: May 26, 2023

(30) Foreign Application Priority Data

May 24, 2023 (EP) .................................... 23174999

(51) Int. Cl.
| | |
|---|---|
| A61L 27/00 | (2006.01) |
| A61F 2/28 | (2006.01) |
| A61F 2/30 | (2006.01) |
| A61L 27/04 | (2006.01) |
| A61L 27/44 | (2006.01) |
| A61L 27/58 | (2006.01) |
| A61L 31/02 | (2006.01) |

(Continued)

(52) U.S. Cl.
CPC ........... *A61L 27/047* (2013.01); *A61L 27/042* (2013.01); *A61L 27/446* (2013.01); *A61L 27/58* (2013.01); *A61L 31/022* (2013.01); *A61L 31/148* (2013.01); *C22C 1/02* (2013.01); *C22C 23/00* (2013.01); *C22F 1/06* (2013.01); *A61L 2420/02* (2013.01)

(58) Field of Classification Search
CPC ...... A61F 2/28; A61F 2/30; A61F 2/07; A61F 2/82; A61L 31/127; A61L 31/022; A61L 27/047
See application file for complete search history.

(56) References Cited

U.S. PATENT DOCUMENTS

| | | | |
|---|---|---|---|
| 9,089,408 B2 * | 7/2015 | Xu | ............................ A61F 2/02 |
| 2013/0261735 A1 * | 10/2013 | Pacetti | ...................... C23C 8/00 |
| | | | 623/1.36 |

(Continued)

FOREIGN PATENT DOCUMENTS

| | | |
|---|---|---|
| CA | 2869459 C | 1/2023 |
| EP | 4023263 A1 | 7/2022 |

OTHER PUBLICATIONS

Extended European Search Report in EP23174999.5, dated Oct. 18, 2023, 8 pages.

*Primary Examiner* — Jason-Dennis N Stewart
(74) *Attorney, Agent, or Firm* — ArentFox Schiff LLP

(57) ABSTRACT

The present application provides an orthopedic implant or a part thereof, comprising biodegradable magnesium alloy comprising magnesium and Ca in the range of 0.550-0.700 wt %, Zn in the range of 0.400-0.700 wt %, and Fe 50 ppm or less, the biodegradable magnesium alloy consisting of two phases comprising a first phase comprising magnesium and Zn and a second phase less noble than the first phase, the second phase comprising $Mg_2Ca$ precipitates larger than nano-sized. The present application also provides a method for preparing the biodegradable magnesium alloy, a method for preparing the orthopedic implant or the part thereof, and a method for treating a subject in need of therapy for a medical condition of a bone.

19 Claims, 6 Drawing Sheets

(51) Int. Cl.
 *A61L 31/14* (2006.01)
 *C22C 1/02* (2006.01)
 *C22C 23/00* (2006.01)
 *C22F 1/06* (2006.01)

(56) References Cited

U.S. PATENT DOCUMENTS

| | | |
|---|---|---|
| 2016/0256208 A1 | 9/2016 | Weinberg |
| 2018/0237895 A1* | 8/2018 | Mueller ................... C22C 23/04 |
| 2020/0139017 A1* | 5/2020 | Meyer-Kobbe ....... A61L 31/028 |
| 2020/0254150 A1* | 8/2020 | Calisse ..................... A61F 2/86 |
| 2022/0296789 A1* | 9/2022 | Lähteenkorva ....... A61L 31/022 |
| 2023/0057929 A1* | 2/2023 | Agudelo Gómez .. A61L 31/127 |

* cited by examiner

IMPLANT COMPRISING MAGNESIUM ALLOY AND A METHOD FOR PREPARING THEREOF

PRIORITY

This application claims priority of European patent application number 23174999.5 filed on May 24, 2023.

TECHNICAL FIELD

The present application relates to implants comprising magnesium alloys and methods for preparing thereof. More particularly the present application relates to magnesium alloys consisting of two phases.

BACKGROUND

Magnesium and alloys thereof are used in medical devices installed into the body, such as implants and the like. Such magnesium materials may contain additional compounds, such as other metals, rare earth metals and other compounds. Some of these compounds are not desired in such materials and may be considered impurities.

Most of the currently used magnesium alloys contain rare earth metals, such as yttrium (Y), gadolinium (Gd) and neodymium (Nd) and this is also the case in the implants commercially available in Europe and Asia. Rare earth metals are added to the alloy to strengthen it, make it more ductile and improve its corrosion behavior. Using rare earth metals in the orthopedic implants however is turned out to be very problematic. They do not naturally exist in the human body. The body has no proper means to get rid of them, so they tend to remain in the body for an extended period or even for an indefinite time. One example of such compound is gadolinium, which has been recently associated with disorders such as nephrogenic systemic fibrosis.

Magnesium may contain other compounds considered as impurities as well. Generally known impurity limits for medical purpose rare earth metal free magnesium alloy are: <30 ppm for Fe, <20 ppm for Cu, <5 ppm for Ni, <200 ppm for Mn, and <200 ppm for Si whereas the total amount of these impurities should be below 400 ppm. Magnesium is prone to corrosion, which is accelerated by galvanic coupling with impurities. Especially iron as an impurity causes localized corrosion of the magnesium material called pitting and has therefore not been desired, especially in medical products and materials.

Iron is usually already present in the raw material used for preparing magnesium alloys. Further, iron is released from steel tools used for processing the alloys, especially when sodium is present.

There is a need to obtain materials with controlled corrosion rate, especially to obtain materials with low corrosion rate and to avoid pit corrosion.

Therefore there is a need to simplify the production process of medical materials and products containing magnesium, and to obtain a variety of less expensive materials and products.

SUMMARY

The present invention overcomes drawbacks of the prior art. It is possible to obtain rare earth metal-free magnesium alloys which exhibit high mechanical strength and low corrosion rate. The amount of certain impurities or otherwise undesired compounds can be maintained at a very low level.

It has been now unexpectedly found against the prior art how to prepare a magnesium alloy with a chemical composition having two phases with a less noble secondary phase, which acts as sacrificial (anodic) site and causes extremely low degradation rate and high mechanical properties even with average and/or maximum grain sizes between 5-15 microns. Also strength retention over normal bone healing period of 6 weeks, even 8 weeks or even more than 12 weeks, was obtained in vivo, which is required for orthopedical medical devices.

The present alloys of magnesium can be prepared with a simple and economical method, and the price of the alloy itself can be kept at a significantly lower level. The method provides advantages over the whole production chain. The obtained stable and low corrosion magnesium alloy can be used in medical applications, such as in implants and the like without the adverse effects due to otherwise too fast, uncontrollable and unpredictable corrosion rate and pitting, which produces cavities to the material and is problematic especially in implants having specific structures such as thin parts and wherein stability and/or controlled and predictable biodegradability is desired.

Further, it was found out that in the two-phase structure, small grain size and low impurity content of the magnesium alloy enhanced the mechanical and corrosion properties of the alloy, so there is no need to include the conventional rare earth metals in such alloys. The presence of iron impurity in the alloy did not have negative impact to the mechanical and corrosion properties of the material and to implants prepared from the material.

Especially it was found that implants prepared from the magnesium alloy exhibited very low cytotoxicity and rather enhanced the viability of cells in contact with the material.

The present application provides an orthopedic implant or a part thereof, such as a core of an implant, comprising biodegradable magnesium alloy comprising magnesium and
 Ca in the range of 0.550-0.700 wt %,
 Zn in the range of 0.400-0.700 wt %, and
 Fe 50 ppm or less,
 the biodegradable magnesium alloy consisting of two phases comprising
 a first phase comprising magnesium and Zn, and
 a second phase less noble than the first phase, the second phase comprising $Mg_2Ca$ precipitates larger than nano-sized.

The present application provides a method for preparing biodegradable magnesium alloy, the method comprising
 providing magnesium alloy comprising
 Ca in the range of 0.550-0.700 wt %, and
 Zn in the range of 0.400-0.700 wt %,
 heating the magnesium alloy to a temperature of 260° C. or more,
 to form the heated magnesium alloy into biodegradable magnesium alloy comprising Fe 50 ppm or less and having an average grain size of 40 μm or less, and consisting of
 a first phase comprising magnesium and Zn, and
 a second phase less noble than the first phase, the second phase comprising $Mg_2Ca$ precipitates larger than nano-sized.

The present application also provides a method for preparing an orthopedic implant or a part thereof, the method comprising
 providing a biodegradable magnesium alloy object having an average grain size of 40 μm or less and comprising magnesium and Ca in the range of 0.550-0.700 wt %,
Zn in the range of 0.400-0.700 wt %, and
Fe 50 ppm or less,
the biodegradable magnesium alloy consisting of
a first phase comprising magnesium and Zn, and
a second phase less noble than the first phase, the second phase comprising $Mg_2Ca$ precipitates larger than nano-sized, and
forming the biodegradable magnesium alloy object into the orthopedic implant or the part thereof.

The present application provides a method for treating a subject in need of therapy for a medical condition of a bone, the method comprising
preferably recognizing a subject in need of treatment or therapy,
providing the orthopedic implant, and
inserting the orthopedic implant into the subject.

The main embodiments are characterized in the independent claims. Various embodiments are disclosed in the dependent claims. The embodiments and examples recited in the claims and in the specification are mutually freely combinable unless otherwise explicitly stated. The examples not claimed in the claims may be examples useful for understanding the invention.

It was found out that when the biodegradable magnesium alloy comprises exactly two phases, the first phase comprising magnesium with diluted zinc acting as a matrix and a second phase comprising $Mg_2Ca$ containing small precipitates, which are larger than nano-sized and can be detected by optical microscopy, and wherein the second phase is less noble than the first matrix phase, the second phase, i.e. the $Mg_2Ca$ precipitates, acts as an internal sacrificial anode, forming a cathodic protection, slowing down the corrosion of the matrix and thus the whole material. Cathodic protection is a known technique used to control the corrosion of a metal surface by less noble (sacrificial site) compound and by making it the cathode of an electro chemical cell. This is especially advantageous when the material is used in an implant inserted in a body. The $Mg_2Ca$ precipitates are small enough and homogenously distributed in the first phase to have no effect on mechanical properties of the material, but as they are larger than nanosized, they can work as a sacrificial site. As the present $Mg_2Ca$ precipitates are distributed homogenously in the biodegradable magnesium alloy, they allow the corrosion to stay under control without detrimental pit-corrosion. These features ensure that the desired mechanical properties are obtained and maintained.

It was found out that if calcium content was 0.55% by weight or more, it ensures that the desired precipitates are formed and not completely dissolving to magnesium in the processing temperatures, which are 260° C. or more. However to avoid formation of a third phase, which would have an adverse effect on corrosion, the calcium content shall be 0.7% or less.

It was found out that when zinc content was 0.4% by weight or more, the mechanical properties of the biodegradable magnesium alloy were improved. However since the zinc content is 0.7% by weight or less, it ensures the all of it to stay diluted in the magnesium matrix.

Too high Zn content is detrimental because of the formation of high amounts of cathodic MgCaZn precipitates. Consequently, reduction of the Zn content is an effective recipe for achieving better biocorrosion resistance. However, it would result in significant loss in strength. Reduction of the Zn-content effect can be easily calculate to be roughly 20 MPa/wt. %, and to compensate the reduced Zn-content fine-grained microstructures (D<5 lm) are required to keep the yield strength at the desired high level, i.e., above 200 MPa. It was found out that the present composition produces yield strength in the required level for the present medical applications i.e., above 200 MPa, even with an average and/or maximum grain size of 5-15 µm and better biocorrosion properties. These and other discussed properties are advantageous for orthopedic implants, especially ones specified in this disclosure.

The obtained composition can be identified by analyzing the $Mg_2Ca$ precipitates as well as the grain size of the magnesium alloy by optical microscopy, as the precipitates are large enough to be visible under an optical microscope.

The present methods provide economical manufacturing of magnesium alloy to medical use when iron free manufacturing devices and contact surfaces are not needed. This is especially useful in manufacturing of the alloy and different types of orthopedic implants.

Such alloy composition of Mg—Zn—Ca has been verified to be biocompatible in in vitro and in vivo testing. All the alloy components are biocompatible and there are substantially no rare earth elements/metals. Preferably the magnesium alloy, and/or the implant, does not contain rare earth elements/metals, such as yttrium (Y), gadolinium (Gd) and/or neodymium (Nd), which may mean that the content thereof is below detection level.

The implant can be prepared with standard techniques, such as by extrusion, but also a variety of other techniques and methods can be applied. No distillation process during the manufacturing of the alloy is needed to remove impurities such as iron, nickel or copper.

The magnesium alloy as a raw material enables using a variety of different preparation methods ranging from conventional mechanical processing methods of metal pieces to injection molding and additive manufacturing methods. A suitable preparation method and device can be selected according to the desired end product and end use. Therefore also a wide variety of different kinds of implants can be obtained from the starting material.

BRIEF DESCRIPTION OF THE FIGURES

FIG. 7A shows IMG1 ($1^{st}$) and FIG. 7B shows Ca—K;

DETAILED DESCRIPTION

Figure 1:
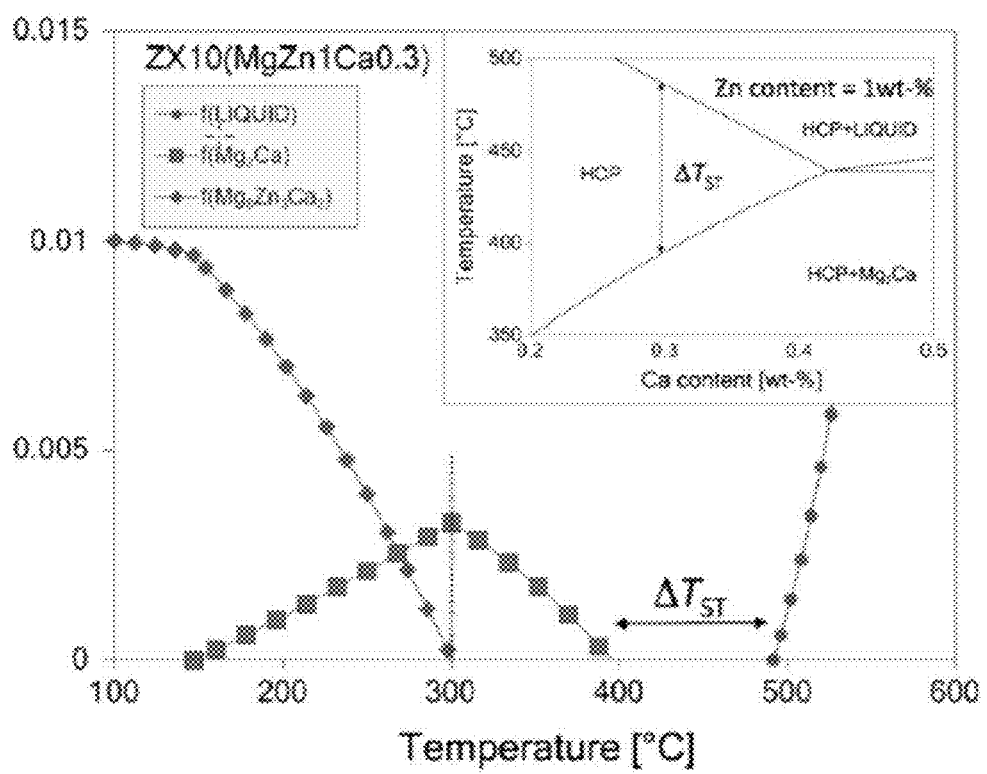
FIG. 1 shows a Mg—Zn—Ca phase diagram of prior art magnesium alloy.

In this specification, if any numerical ranges are provided, the ranges include also the upper and lower values. The open term "comprise" also includes a closed term "consisting of" as one option. The dimensions disclosed herein can be detected microscopically, such as by using optical microscopy, for example from microscopy images. The images may be analyzed using a dedicated software, which may be provided by the microscopy manufacturer, such as to determine the dimensions and/or size distribution from an image.

Unless defined otherwise, all technical and scientific terms used herein have the same meaning as commonly understood by one of ordinary skill in the art to which the invention belongs.

In this specification, except where the context requires otherwise, the words "comprise", "comprises" and "comprising" means "include", "includes" and "including", respectively. That is, when the invention is described or defined as comprising specified features, various embodiments of the same invention may also include additional features.

The percentages presented herein are weight percentages, unless otherwise indicated. The phrases "weight percent", "percent by weight", "by weight", "% (w/w)" and "wt %" may be used interchangeably and are intended to denote the percent by weight based on the total expressed composition, unless otherwise explicitly stated.

The term "biodegradable" refers to material which, when in contact with biological environment, will degrade and/or decompose, either fully or partially. The degradation may be caused or accelerated by the biological environment, and it may be controlled by selecting suitable composition and properties of the material. The biological environment may refer to a body, such as one or more parts and/or tissues of body which are implantable with the present implants, for example bone, cartilage and/or other associated tissues or other body parts. The materials may be fully biodegradable in a body.

The term "bioresorbable" refers to material, such as metals or alloys thereof, polymers, glass and/or ceramics, which in contact with biological environment such biological tissues and/or physiological fluids will, following placement, degrade, resorb and/or absorb into the environment, either fully or partially, while maintaining its mechanical properties for a certain period of time. More particularly "bioresorbable", for example in context with metals or alloys thereof, glass and/or ceramics, may refer to such materials which degrade safely within the body. The materials may be fully bioresorbable in a body.

The terms "bioresorbable", "biodegradable", "biosoluble", "bioabsorbable", biocorridible and "bioerodible", with or without prefix "bio", are often used interchangeably, and the terms may at least overlap. If applicable, the terms may be used interchangeably also herein. However the term "biodegradable" is intended to cover all the other terms as it does not specify the type of degradation or what will happen to the degradation products in the biological environment. The "biodegradable" may refer to biodegradable in body and/or biodegradable in contact with (biological) tissue and/or body tissue.

The terms "bioresorbable glass fiber", "bioresorbable fiber", "bioglass fiber", "controlled lifetime glass fiber", "alterable glass fiber", "glass fiber", and "fiber" may be used interchangeably herein.

The term decomposability may be defined here as (biology) to break down (organic matter) or (of organic matter) to be broken down physically and chemically; (chemistry) to break down or cause to break down into simpler chemical compounds or to break up or separate into constituent parts. Degradability may refer to the state or quality of being susceptible to breakdown or decomposition.

Herein and hereafter "optional" or "optionally" denotes that the subsequently described event or circumstance may but need not occur, and that the description includes instances where the event or circumstance occurs and instances in which it does not. "Comprises" or "comprising" denotes that the subsequently described set may, but need not, include other elements.

The present application provides a medical device, such as an implant or part thereof, comprising magnesium alloy. The magnesium alloy in the medical device may be present as such and/or it may be present as composite material together with one or more further material(s).

The implant may be any suitable medical device which is designed, arranged and/or intended to be inserted into living tissue, either fully or partially, such as into a body, for example into a bone. The implant may be used for bone-to-bone, soft tissue-to-bone, soft tissue-into-bone and/or soft tissue-to-soft tissue fixation. The implant is biocompatible with living tissue. The implant, or at least the magnesium alloy therein, may be biodegradable, such as fully biodegradable. The implant may be or may be provided in the form of an orthopedic implant, for example a bone implant. The implant may or may not contain other parts in addition to a part comprising or consisting of the magnesium alloy disclosed herein. The optional other part(s) may or may not be biodegradable. However fully biodegradable implants are preferred for the present uses. The properties of the present magnesium alloys and object formed from the magnesium alloy are especially suitable for orthopedic implants, which benefit the enhanced mechanical and chemical properties of the material, such as bending and shear strength, elasticity, controlled and predictable biodegradability, and other properties disclosed herein.

Magnesium is considered biocompatible, biodegradable, bioresorbable and non-toxic and has been shown to increase the rate of bone formation i.e. to be osteopromotive, because magnesium is also an important ion in the formation of the biological apatites that make up the bulk of bone mineral, a key part to new bone formation. Therefore, magnesium can be classified as bioactive material. Magnesium is also known to have a positive influence on bone fragility and strength.

A problem with biocompatible medical devices and materials is the difficulty of controlling the corrosion of the material. The corrosion may be caused by several factors, including presence and content of impurities, presence of different phases and/or presence of nanosized precipitates, which may have adverse effects to the properties of the material. This is the case especially in magnesium-based alloys, wherein very small changes in the content of alloying compounds may have a great effect to the properties of the alloy. For example it was found in the present invention that the calcium content has a great impact to the formation of phases in the alloy.

In prior art solutions, wherein the zinc and calcium content is low, complete dissolution of the alloying elements occur and no second phase remains after a heat treatment. Such solutions may also aim to obtain nanosized precipitates, which are not visible under an optical microscope. Such precipitates are less noble that the magnesium matrix and have no three dimensional connectivity among themselves. Such precipitates also prevent the grains from coarsening, so that fine grain size of less than 5 micrometers is obtained after extrusion. The $Mg_2Ca$ is present in a single phase in such a low concentration that it is not visible by optical microscopy.

Figure 2:
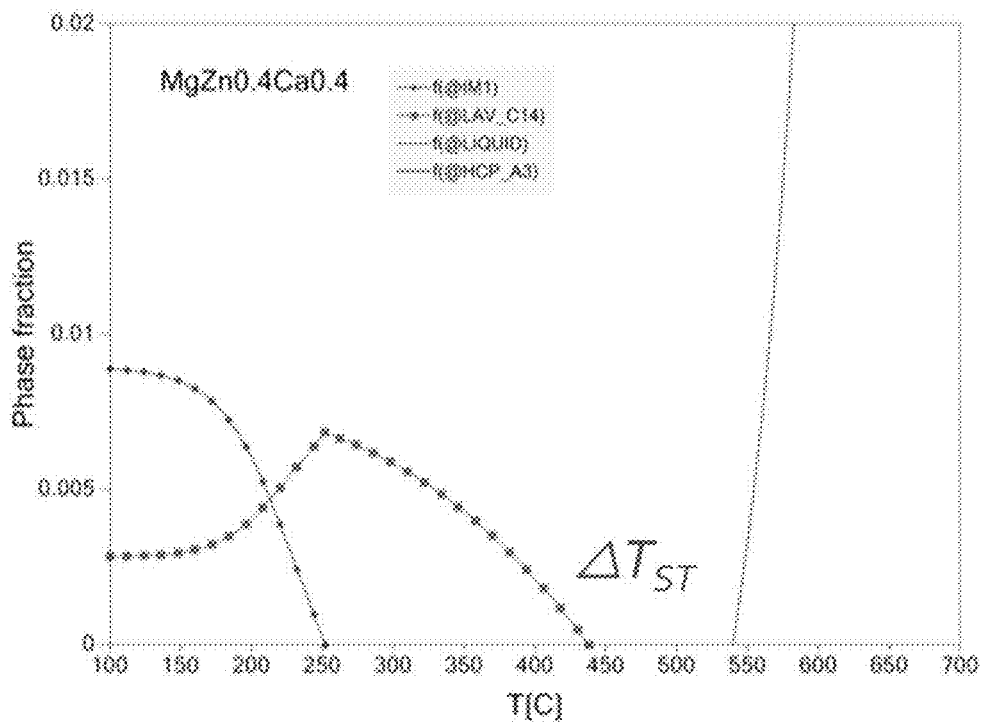
FIG. 2 shows a Mg—Zn—Ca phase diagram of the present magnesium alloy comprising 0.4% by weight zinc and 0.4% by weight calcium.
Figure 3:
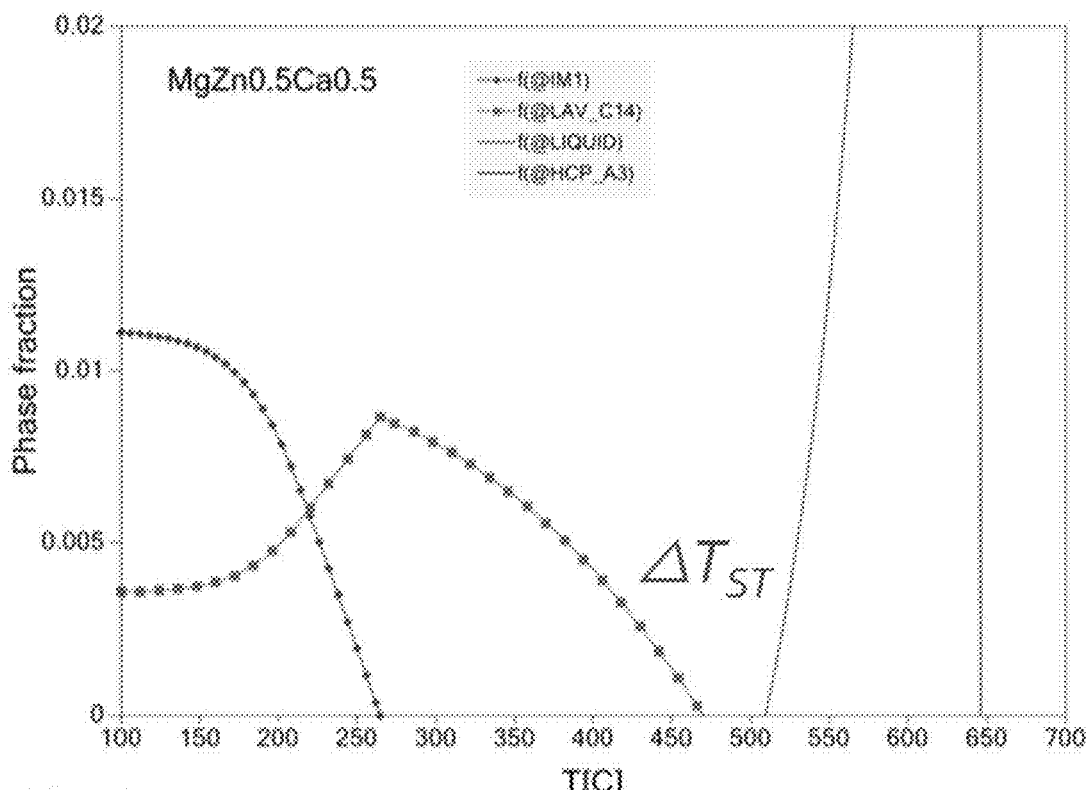
FIG. 3 shows a Mg—Zn—Ca phase diagram of the present magnesium alloy comprising 0.5% by weight zinc and 0.5% by weight calcium.

FIGS. 1-4 demonstrate the effect of zinc and calcium content as well as the importance of the formation temperature to the final properties of magnesium alloys with Mg-Za-Ca phase diagrams. FIG. 1 shows phase diagrams determined for prior art magnesium alloy comprising 1 wt % zinc and 0.3 wt % magnesium. $\Delta T_{ST}$ is the temperature range where only one phase exists in relation to Ca content and with solution heat treatment making possible only nanosized precipitates to form. FIGS. 2 and 3 show the presence of $\Delta T_{ST}$, with the amounts of calcium and zinc in the range of 0.4-0.5 wt % in magnesium alloy. No second phase exists with these calcium ranges.

Figure 4:
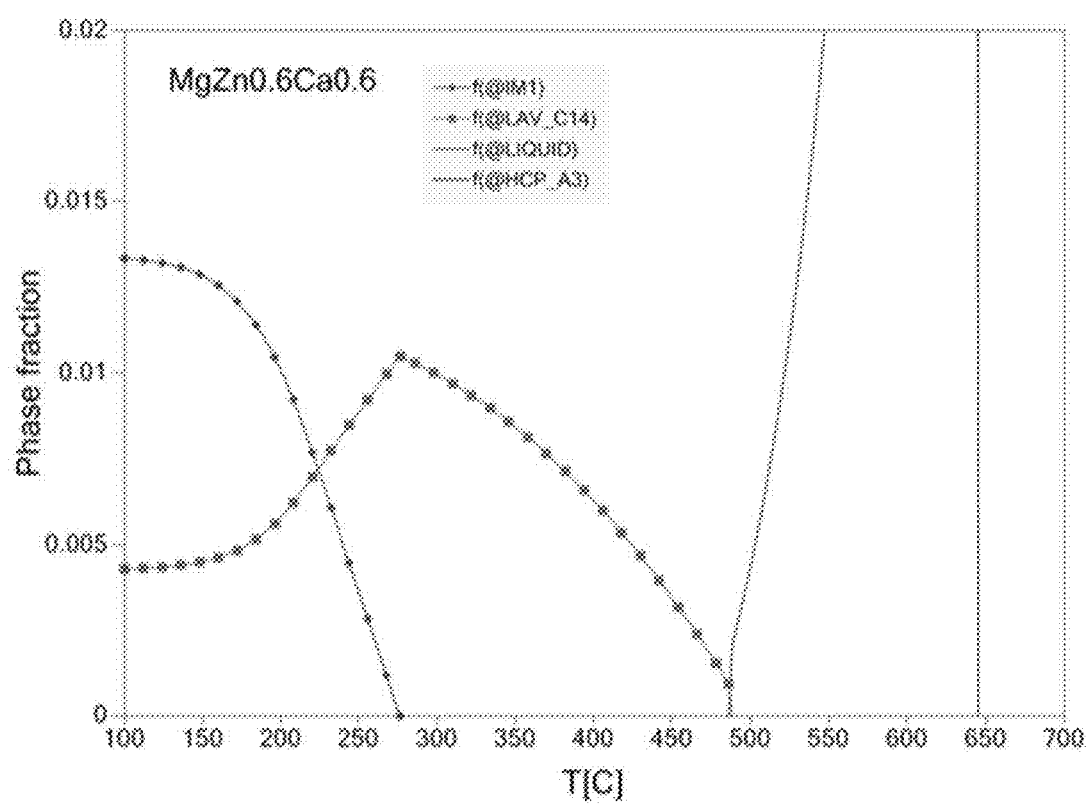
FIG. 4 shows a Mg—Zn—Ca phase diagram of the present magnesium alloy comprising 0.6% by weight zinc and 0.6% by weight calcium.

FIG. 4 shows phase diagram for present magnesium alloy comprising 0.6 wt % zinc and 0.6 wt % calcium. No $\Delta T_{ST}$ exists but $Mg_2Ca$ second phase exists above calcium content of 0.55 wt %. With the chemical composition containing calcium in the range of 0.550-0.700 wt % and zinc in the range of 0.400-0.700 wt %, only $Mg_2Ca$ can be considered for thermodynamic reasons in the temperature range of extrusion forming, i.e. T>250° C. At such conditions it was possible to obtain biodegradable magnesium alloy consisting of two phases comprising a first phase comprising magnesium and Zn, and a second phase less noble than the first phase, the second phase comprising $Mg_2Ca$ comprising precipitates which are larger than nano-sized and thus visible under optical microscope.

Therefore in the present invention it was recognized, that for the present types of implants it was advantageous to prepare magnesium alloy containing exactly the two phases. Also the conditions required for obtaining the two phases were recognized and applied in the preparation of the implants or implant material.

The problems discussed herein are especially pronounced in medical devices such as implants, especially orthopedic implants, which have specific structures and are intended in specific uses in demanding environment. Preparation of such devices may include specific challenges.

The present application provides a method for preparing biodegradable magnesium alloy, the method comprising
providing magnesium alloy comprising
Ca in the range of 0.55-0.70 wt %, and
Zn in the range of 0.40-0.70 wt %,
heating the magnesium alloy to a temperature of more than 250° C., such as 255° C. or more, preferably 260° C. or more to ensure obtaining the two phases,
forming the heated magnesium alloy into biodegradable magnesium alloy comprising Fe 50 ppm or less and having an average grain size of 40 µm or less, and consisting of
a first phase comprising magnesium and Zn, and
a second phase comprising $Mg_2Ca$ precipitates larger than nano-sized and/or visible by optical microscopy. Preferably the second phase, which is less noble than the first phase, comprises $Mg_2Ca$ precipitates larger than nano-sized.

"Larger than nano-sized" as used herein refer to size and/or structures, which are visible by optical microscopy. The average smallest diameter of larger than nano-sized may be about one or two micrometer(s) or more, such as in the range of 1-20 micrometers (µm), 2-20 micrometers, preferably 5-20 micrometers, more preferably 5-15 micrometers. In the present materials this also excludes the presence of substantial amounts of nano-sized structure, so the majority of the discussed precipitates are larger than nano-sized, such as at least 90% by number or volume, or at least 95%, at least 98% or at least 99%. The second phase may consist of or substantially consist of the $Mg_2Ca$ precipitates larger than nano-sized. The desired mechanical strength can be achieved without the need to pin grain size below 5 microns.

In one embodiment the method comprises heating the magnesium alloy to a temperature of 260° C. or more, such as 270° C. or more, for example 300° C. or more. The magnesium alloy may be heated to a temperature in the range of 260-400° C., such as 270-400° C.

In the forming of the heated magnesium alloy into biodegradable magnesium alloy the two phases are formed, impurities present in the starting material(s), such as in the initial magnesium alloy are removed, and the grain size of 40 µm or less is formed. Preferably the second phase comprising $Mg_2Ca$ includes no or substantially no impurities.

One embodiment provides a biodegradable magnesium alloy consisting of magnesium and
Ca in the range of 0.500-0.700 wt %, such as 0.550-0.700 wt %,
Zn in the range of 0.400-0.700 wt %, such as 0.400-0.600 wt %, and
Fe 50 ppm or less,
the biodegradable magnesium alloy consisting of two phases comprising
a first phase comprising magnesium and Zn, and
a second phase less noble than the first phase, the second phase comprising $Mg_2Ca$ precipitates. The precipitates are larger than nano-sized, i.e. they are detectable by optical microscopy. The $Mg_2Ca$ precipitates may refer to precipitates comprising $Mg_2Ca$ or consisting of $Mg_2Ca$.

Disclosed is an implant and/or a part of the implant comprising or consisting of the biodegradable magnesium alloy. The implant, when discussed in respect of the biodegradable magnesium alloy only, may refer to a magnesium alloy part of a composite implant, such as a core of a composite implant.

The initially provided magnesium alloy mixture may already comprise iron and/or iron may be accumulated to the alloy in the process, for example from the equipment. It is however desired to keep the Fe content low, even lower than said 50 ppm, such as 40 ppm or less, 30 ppm or less or preferably 20 ppm or less. Therefore Fe is not present in a separate phase, such as a Fe-phase or a phase comprising or consisting a complex of Fe and another agent, such as zirconium. This enables obtaining the biodegradable magnesium alloy consisting of two phases only, which has impacts to the mechanical and chemical properties of the alloy.

In one embodiment the biodegradable magnesium alloy comprises Fe less than 40 ppm or less, such as 30 ppm or less, preferably 20 ppm or less. It is possible to obtain pure magnesium alloy having such a low Fe content, even 10 ppm or less, even without complexing agents or with a very low amount of complexing agent, such as zirconium, such as with 10 ppm or less, or 5 ppm or less, complexing agent.

A fundamental characteristic measure for microstructures of metallic materials is the average grain size, which may be determined for example by using linear intercept method, such as ASTM E1382 linear intercept method. A suitable software may be used to analyze microscopic images and to calculate and provide the average grain size. The grain size may be also determined and provided as volume-weighted average grain size.

The grain size, such as average grain size, may be determined as equivalent circular diameter (ECD), for example microscopically. An average gran size may be 40 µm or less, such as 30 µm or less, preferably 20 µm or less, 10 µm or less or 5 µm or less. However the minimum grain size may be 2 µm or more, 3 µm or more, 4 µm or more, or 5 µm or more. Most of the grains may be in a range of 2-20 µm, but a portion of grains may be larger as having a grain size of 5 µm or more. The grain size distribution can be used to identify the present magnesium alloy.

In one embodiment the biodegradable magnesium alloy has an average grain size determined as equivalent circular diameter (ECD) of 2-20 µm, wherein at least 10%, such as at least 15%, even at least 20%, of grains have a grain size above 5 µm. In one example the biodegradable magnesium alloy has an average grain size determined as equivalent circular diameter (ECD) of 2-10 µm, wherein at least 10%, such as at least 15%, of grains have a grain size above 5 µm. The percentages may be determined by area fraction, wherein the grains with EDC above the discussed µm value cover said percentage of the measured total area.

The magnesium alloy, or the implant or the part of the implant, may comprise
Fe 20 ppm or less, and
total impurities including Fe in the range of 100-1000 ppm. Preferably the magnesium alloy has an average grain size by area fraction (ECD) of 2-20 µm with at least 10% having a grain size above 5 µm. This may also refer to maximum grain size.

In one embodiment the biodegradable magnesium alloy, or the implant or part of the implant, consists of or substantially consists of magnesium and
Ca in the range of 0.550-0.700 wt %,
Zn in the range of 0.400-0.600 wt %.

In one embodiment the biodegradable magnesium alloy, or the implant or part of the implant, consists of or substantially consists of magnesium and
Ca in the range of 0.5500-0.7000 wt %,
Zn in the range of 0.4000-0.6000 wt %.

In one embodiment the ratio of weight percentages Ca:(Zn-0.2) is 1.1 or more, such as 1.2 or more. With this ratio the low amount of zinc allows it to be soluble in the alloy so that it does not form an additional phase, and the amount of calcium is high enough to form the second, less noble phase.

The magnesium alloy preferably comprises total impurities in the range of 100-1000 ppm, the impurities including Fe. Other impurities may include any other compound(s), such as mentioned herein, such as one or more of Al, Cu, Fe, Mn, Si, Y, Zr, Cd, Pb, Ni, Co, V, Li, Sb and/or (other) rare earth elements. In one embodiment the magnesium alloy comprises total impurity, i.e. total amount, of Al, Cu, Fe, Mn, Si, Y, Zr, Cd, Pb, Ni, Co, V, Li, Sb and (other) rare earth elements below a detection level, which is 1000 ppm or less, such as 800 ppm or less, 600 ppm or less, 400 ppm or less, or even 200 ppm or less. However in most cases the magnesium alloy comprises an amount of total impurities, such as 300 ppm or more, or 400 ppm or more, up to 800 ppm or 1000 µm, which are tolerable in most cases in orthopedic implants. Total impurities may be present in the range of 100-800 ppm, 100-600 ppm, 200-800 ppm, 200-600 ppm, 300-1000 ppm, 400-8000 ppm or 400-1000 ppm.

A single impurity may be present in an amount of 100 ppm or less, such as 50 ppm or less, or 20 ppm or less. For example zirconium content may be 50 ppm or less, such as 20 ppm or less, even 10 ppm or less.

It is desired that the magnesium alloy contains as little as possible rare earth metals/elements. The rare earth elements (REE), also called the rare earth metals or rare earths or, in context, rare earth oxides, and sometimes the lanthanides (although yttrium and scandium, which do not belong to this series, are usually included as rare earths), are a set of 17 nearly indistinguishable lustrous silvery-white soft heavy metals, namely lanthanum, cerium, praseodymium, neodymium, promethium, samarium, europium, gadolinium, terbium, dysprosium, holmium, erbium, thulium, ytterbium, lutetium, scandium, and yttrium.

On one embodiment the magnesium alloy and/or the implant does not contain rare earth metals/elements, such as yttrium (Y), gadolinium (Gd) and/or neodymium (Nd), or contains them in trace amount only, such as in amounts disclosed herein, for example 0.0200% or less, 0.0100% or less, 0.070% or less, or 0.050% or less (percentages by weight).

The processed magnesium alloy may be formed into an object, which may be an elongated object, for example by using methods or processes disclosed herein, for example plastic deformation. The biodegradable magnesium alloy object discussed herein may refer to an object comprising or consisting of the biodegradable magnesium alloy. An implant, a part of an implant or a blank for an implant or for a part of an implant, which blank is an intermediate product, may be obtained. The processed magnesium alloy may also be formed into an object having another shape, such as a plate or a sheet, or the elongated object may be further processed into a different form. The expression "implant" used herein may also be considered including "part of the implant".

The method for preparing the implant, or the part of the implant, disclosed herein comprises
providing magnesium alloy having an average grain size of 40 µm or less and comprising magnesium and
Ca in the range of 0.550-0.700 wt %,
Zn in the range of 0.400-0.700 wt %, and
Fe 50 ppm or less,
the biodegradable magnesium alloy consisting of
a first phase comprising magnesium and Zn, and
a second phase less noble than the first phase, the second phase comprising $Mg_2Ca$ precipitates larger than nano-sized, preferably as the object disclosed herein, and
forming the magnesium alloy, such as the object, into an implant or part of an implant.

The manufacturing process of an implant or a part thereof comprising magnesium alloy usually comprises process steps such as casting, extrusion, machining and heat treatment.

In one example the present magnesium alloy is cast according to the following steps, such as according to all or most of the steps:

1. Melting: The first step in casting magnesium alloys is to melt the raw materials in a furnace, such as in temperature between 650° C. and 750° C. The raw materials include magnesium and alloying elements such as calcium and zinc.
2. Degassing: Once the alloy has been melted, it may be degassed to remove any impurities or gases that may have been trapped in the melt. This can be done using a combination of vacuum and/or inert gas to remove the impurities.

3. Fluxing: Fluxing may be carried out by adding a compound to the melt to remove any remaining impurities and to protect the surface of the melt from oxidation.
4. Mold preparation: The mold used for casting may be prepared by cleaning and coating it with a mold release agent to prevent the molten metal from sticking to the mold.
5. Pouring: The molten magnesium alloy may be poured into the prepared mold and left to cool and solidify.
6. Removal: Once the casting has solidified, it is removed from the mold. The casting may need to be cleaned and finished to remove any excess material or surface imperfections.
7. Heat treatment: The casting may undergo a heat treatment process to further improve its mechanical properties.
8. Machining: Finally, the casting may be machined to its final shape and size (billet), ready for the extrusion step.

In one example the magnesium alloy casting from example 1 is extruded according to the following steps:
1. Billet Preparation: The first step is to prepare the billet, which is the starting material for the extrusion process. The billet may be made by melting the magnesium alloy and casting it into a desired shape, such as a cylindrical shape.
2. Preheating: The billet is heated to a temperature slightly below the melting point of the magnesium alloy. This preheating step softens the material and makes it easier to extrude.
3. Extrusion: The preheated billet is placed in the extrusion press and forced through a die. The die may be made of steel and it may have a cylindrical cross-sectional shape and the used extrusion temperature may be between 400° C. and 450° C. The pressure applied to the billet causes it to flow through the die and take on the shape of the die opening, such as a cylindrical shape.
4. Cooling: The extruded profile is then cooled by air or water. This cooling step helps to harden the magnesium alloy and set the shape of the extruded profile.
5. Cutting: Once the extruded profile has cooled, it is cut to the desired length using a saw or other cutting tool.
6. Finishing: The final step is to finish the extruded profile/billet by removing any sharp edges or surface defects. This may be done using one or more of sanding, grinding, and polishing.

In one example the magnesium alloy profile/billet is machined according to the following steps:
1. Profile/billet incoming inspection.
2. Machining implants with a CNC using carbide and TiAl-nitride coated tools without any processing aids.
3. The conformity of the manufacturing process is verified by sampling critical dimensions.
4. Implant cleaning with a 100% ethanol
5. Implant drying in a controlled environment.
6. Implant packaging
7. Implant heat treatment, such as 2 hours in 160° C. to 180° C.
8. Final inspection of the implants A provider of magnesium alloy, who may be considered as a first operator, may carry out the first part of the process, wherein the initial magnesium alloy comprising Ca in the range of 0.550-0.700 wt % and Zn in the range of 0.400-0.700 wt % is prepared and/or provided. This operator, or another operator, may carry out the heating process comprising heating the magnesium alloy to a temperature of 260° C. or more, and forming the heated magnesium alloy into biodegradable magnesium alloy comprising Fe 50 ppm or less and having an average grain size of 40 μm or less and consisting of the two phases.

The prepared biodegradable magnesium alloy may be then recovered and provided to medical device manufacturing, for example as intermediate objects, which may be the elongated objects discussed herein or other applicable objects. The processed magnesium alloy or the objects or products comprising thereof may be packed and transported to the implant manufacturer or other applicable product manufacturer who can utilize and further process the material. The processed magnesium alloy is in such a form which tolerates prolonged storing, handling and transporting of the material, so products with good quality can be prepared from the material. This manufacturer may be another (second) operator who may carry out the processing of the processed magnesium alloy and/or the objects.

However the magnesium alloy may comprise a non-uniform initial grain structure comprising large columnar grains growing in the direction of solidification. Such material may be brittle with weak grain boundaries and may contain defects such as shrinkage cavities, porosity caused by gases, and foreign material such as metallic oxides. It is possible to form or deform such material into more uniform structure exhibiting higher toughness, strength, ductility and resistance to vibration and shock. Also such deformed form exhibits better formability into implants. In such process the magnesium alloy is formed into an object having a specific grain size.

The present method may comprise heating the magnesium alloy, which may be called a heat treatment or forming or deforming treatment. The process preferably comprises deforming the magnesium alloy. The heating is carried out at a temperature high enough to obtain a plasticly deformable form and/or grain refinement. The magnesium alloy may be heated above the recrystallization temperature of the magnesium alloy to be able to plastically deform it in a suitable working operation. The obtained magnesium alloy may be then subjected to one or more working operation(s), which may be carried out with suitable method(s) and device(s), such as by extrusion, rolling, drawing and/or forging, which may be called plastic deforming operation, process or step. The process can also be characterized as a grain-refinement operation, process or step. The process may be or comprise a cold drawing or a cold deforming process. In such process a specific grain size of the material is obtained and can be controlled. This step can be carried out by a first operator, such as the manufacturer and/or the provider of the magnesium alloy, or it can be carried out by a second operator, such as the implant manufacturer. The process chain may also include more operators, which each may carry out one or more of the process steps discussed herein.

The elongated object may refer to any object which has been deformed in such way that the length of the material at least in one direction is increased. The elongated object may be a rod, a tube but also a plate, a sheet, a fiber, a filament, a wire or the like object, having a rod-like form, tube-like form, plate-like form, sheet-like form, fiber, filament or wire like form, or other similar or applicable form.

In one example the processing is carried out by using a suitable extruder so that an elongated object is formed. In one example the processing is carried out by rolling, more particularly by hot rolling.

In one embodiment the magnesium alloy has an average grain size of 40 μm or less. The grains refer to grains of the same material, i.e. the magnesium alloy as a whole, which is different from the phases discussed herein. The (plastic) deformation treatment and/or grain refinement process, and optional second heat treatment, enable obtaining the small average grain size of 40 μm or less, or 30 μm or less, or even 20 μm or less, which is considered as an indication of the high quality of the obtained magnesium alloy as well as a feature indicating the production process thereof. Such magnesium alloy having an average gran size of 40 μm or less was found to provide enhanced bending strength, shear strength and elastic modulus compared to untreated magnesium alloy, but especially an average grain size of 20 μm or less provided even better bending strength, shear strength and elastic modulus as shown in FIG. 3. The average grain size may be in the range of 1-40 μm, such as 5-40 μm, 10-40 μm, 1-30 μm, 5-30 μm, or 1-20 μm or 5-20 μm. In the tests it was found out that ideally the grain size should be 20 μm or less, but already a magnesium alloy having a grain size of 40 μm was useful for most applications. The smaller grain size correlated with predictable corrosion rate, so especially for biodegradable implant use it is desired to obtain a grain size of 40 μm or less, as disclosed herein. The grain size may be presented as an average grain size or a maximum grain size. The grain size may be determined microscopically, for example by using optical microscopy or electron microscopy, such as scanning electron microscopy (SEM).

Optical microscopy can be carried out with any suitable method. The samples to be studied may be pretreated, such as etched, for example by using the following etching method. Two etching solutions are prepared. Etching solution 1 comprises 100 ml ethanol and 5.6 g of picric acid. Etching solution 2 comprises 5 ml of acetic acid and 5 ml deionized water.

The final etching solution is prepared by combining 40 ml of solution 1 and 10 ml of solution 2. Samples are polished with an oxide polishing suspension (+ammonia), cleaned and subsequently immersed in the etching solution for about 5-10 seconds. The samples are cleaned with isopropanol and dried.

This etches the grain boundaries and with polarized light the grains can easily be distinguished. The average grain sizes can be determined from microscopic images.

The obtained magnesium alloy object can be formed into a desired shape, especially into an implant or any other applicable medical device, or into a different form.

The magnesium alloy, such as an object obtained from the magnesium alloy, may be provided in any suitable form and/or processed into such form, such as solid pieces, chips, powder, granules, wire or the like, or formed into such form.

The present application provides a method for preparing an implant or a part of the implant, the method comprising
providing a biodegradable magnesium alloy object having an average grain size of 40 μm or less and comprising magnesium and
Ca in the range of 0.550-0.700 wt %,
Zn in the range of 0.400-0.700 wt %, and
Fe 50 ppm or less,
the biodegradable magnesium alloy consisting of
a first phase comprising magnesium and Zn, and
a second phase less noble than the first phase, the second phase comprising $Mg_2Ca$ precipitates larger than nano-sized, and
forming the object into the implant or into the part of the implant. The biodegradable magnesium alloy, which is the processed magnesium alloy, may be obtained from the preparation method disclosed herein.

In one embodiment the method comprises
providing biodegradable magnesium alloy comprising
Ca in the range of 0.550-0.700 wt %,
Zn in the range of 0.400-0.700 wt %,
heating the magnesium alloy to a temperature of at least 260° C.,
to form the heated magnesium alloy into a biodegradable magnesium alloy object consisting of two phases comprising
a first phase comprising magnesium and Zn, and
a second phase less noble than the first phase, the second phase comprising $Mg_2Ca$ precipitates larger than nano-sized,
the biodegradable magnesium alloy comprising Fe 50 ppm or less and having an average grain size of 40 μm or less One example provides a method for preparing a medical device, such as an implant, preferably an orthopedic implant, or a part thereof, the method comprising
providing biodegradable magnesium alloy, for example as an object, preferably elongated object, the magnesium alloy comprising magnesium
Ca in the range of 0.550-0.700 wt %,
Zn in the range of 0.400-0.700 wt %, and
Fe 50 ppm or less,
the biodegradable magnesium alloy consisting of
a first phase comprising magnesium and Zn, and
a second phase less noble than the first phase, the second phase comprising $Mg_2Ca$ precipitates larger than nano-sized, and
forming the magnesium alloy, or the object, into a medical device, such as an implant or a part of the implant. Preferably the biodegradable magnesium alloy has an average grain size of 40 μm or less.

As discussed in previous, this manufacturing process can be carried out for the initial magnesium alloy to obtain a desired grain size, plastic deformation and/or gran refinement of the magnesium alloy. This process can be carried out before packing, storing and/or transporting the material, so that objects which tolerate handling, packing, storing and/or transporting are obtained. This can be carried out for example by the magnesium alloy manufacturer or provider, which can be for example a first or second operator in the production chain. Such an operator can therefore prepare in intermediate product having good quality and for example high dimension accuracy. The intermediate product can be provided to another operator in such form that has not damaged or degraded during handling, packing, storing and/or transporting, and which can be easily further processed, for example by using any of the methods disclosed herein, and implants with good quality can be obtained. For example the intermediate product may be an elongated product, such as an rod or a tube, which has high dimensional accuracy and desired precision.

One embodiment provides a method for preparing an implant or a part of an implant, the method comprising
providing biodegradable magnesium alloy comprising
Ca in the range of 0.550-0.700 wt %,
Zn in the range of 0.400-0.700 wt %,
heating the magnesium alloy to temperature of 260° C. or more, for example to 260-400° C.,
forming the heated magnesium alloy into an object having an average grain size of 40 μm or less, and
forming the object into the implant or part of the implant.

In one embodiment the heating and forming the magnesium alloy comprises heating the magnesium alloy to a temperature of 260° C. or more and extrusion forming the heated magnesium alloy into the object having the average grain size of 40 μm or less.

The present application discloses use of said magnesium alloy, or use of an object comprising said magnesium alloy, for preparing an implant, such as an implant disclosed herein with a method disclosed herein.

The method may comprise an additional (second) heat treatment either before or after the implant forming step by keeping the Mg-alloy at 160-200° C., preferably 160-180° C., for 30-120 minutes. This second heat treatment has an impact on the grain size of the material, and to the mechanical properties of the material and the implants obtained from the material. As shown in FIG. 2, the heat treatment at the range of 160-180° C. provides especially increased bending strength, shear strength and elastic modulus. This heat treatment is separate from the heat treatment carried out at the plastic deformation/grain refining step, and is carried out after the plastic deformation/grain refining.

The heat treatment(s) may provide suitable dry heat sterilization of the magnesium alloy, which may be required for medical implants. However the second heat treatment may be carried out at different location and/or by different operator than the first heat treatment, and it can be carried out especially to obtain the dry heat sterilization effect. The dry heat sterilization may be carried out by using any suitable heating device or means, such as a specific dry heating device. This can be carried out for example by the implant manufacturer.

In one example the method comprises heating the biodegradable magnesium alloy, which may be in the form of the object, at 160-180° C. for at least 30 minutes, such as 30-180 minutes, for example 30-120 minutes, before and/or after forming the biodegradable magnesium alloy into the implant. In one embodiment the method comprises heating the implant at 160-180° C. for at least 30 minutes, such as 30-180 minutes, for example 30-120 minutes.

The provided magnesium alloy or the object is formed into the implant by using a suitable forming or processing method(s) and/or device(s). Different methods and devices may be applied depending on the desired end product and/or end use. Forming the object into an implant may or may not include substantial processing. In some cases the object may be already in a suitable form after previous process steps, so it may be necessary merely to clean, polish, pack and/or carry out other minor actions to obtain the final product, which is the implant, preferably ready to be used.

In one embodiment the forming the object into the implant or the part thereof comprises processing the object with one or more of the following:
mechanical machining,
laser machining,
wroughting,
water jet processing,
additive manufacturing, such as comprising providing the biodegradable magnesium alloy as powder, granules or as a wire, and
injection molding,
to form the implant.

The present disclosure provides an implant or part of the implant obtained with any of the methods disclosed herein.

The implant may have a tensile strength of 260 MPa or more, determined according to ASTM B557M-15 Standard Test Methods for Tension Testing Wrought and Cast Aluminum- and Magnesium-Alloy Products.

The implant may have a yield strength of 200 MPa or more, determined according to ASTM B557M-15 Standard Test Methods for Tension Testing Wrought and Cast Aluminum- and Magnesium-Alloy Products.

The implant may have an elongation at fracture of 10% or more, determined according to ASTM B557M-15 Standard Test Methods for Tension Testing Wrought and Cast Aluminum- and Magnesium-Alloy Products.

The processing may include one or more processing steps that modify the shape of the object towards the shape of the implant, i.e. to obtain the desired shape of the final product or part thereof. Instead of implant the method may be used to produce another applicable medical device, or other device or object, or a part thereof.

Mechanical machining may comprise processing the object with one or more machining means which remove material from the object and/or change the shape of the object, for example bend the object. Machining means may comprise one or more machine tools, for example tools for forming one or more thread, groove or the like form(s) to the object, and/or other means such as pressing means.

Laser machining, such as laser beam machining, comprises processing the object with laser energy. The laser may be provided by one or more source(s) of laser, such as a gas laser, a solid state laser or an excimer.

Wroughting by any suitable process, such as by forging, swaging, hammering may be used to process the magnesium alloy.

Wroughting refers to processing the object in solid form through one or several processing steps and it may comprise different type of molding, shaping and/or manufacturing steps, such as pressure compression molding and/or profile or sheet extrusion. Wroughting may comprise heating and working with one or more tools(s) and/or machine(s). A wrought object is obtained.

Swaging is a metal-forming technique in which the metal of one part is deformed to fit around another part by either pressing or hammering, or by forcing the material through a die. Swaging differs from forging in that the swaged metal is cold worked and the output of the swaging operation is usually the finished shape.

Additive manufacturing, also known as 3D printing, may comprise processing the biodegradable magnesium alloy with additive manufacturing means. The biodegradable magnesium alloy may have been formed into a desired form suitable as raw material or starting material for additive manufacturing, such as powder, chip, granule or wire form.

This form has the composition of the biodegradable magnesium alloy disclosed herein, but it has been processed to a form which is compatible with the additive manufacturing means. Therefore the method may comprise providing the magnesium alloy in a suitable form, such as powder, chip, granule or wire form. Such forms may be used in other manufacturing methods as well, when applicable.

Additive manufacturing means suitable for processing metal may be used. ISO/ASTM52900-15 defines seven categories of additive manufacturing processes within its meaning: binder jetting, directed energy deposition, material extrusion, material jetting, powder bed fusion, sheet lamination, and vat photopolymerization. Usually additive manufacturing methods comprise forming the object layer-by-layer, i.e. depositing the material to add a layer and repeating this.

The method may comprise providing a computer-stored 3D model of the object to be manufactured. The 3D model is then used to control the additive manufacturing means to create an object according to the 3D model.

In certain methods the material is melt or soften to produce layers. One example is Fused filament fabrication, also known as Fused deposition modeling (FDM), wherein the object is produced by extruding small beads (granules) or streams of material which harden immediately to form layers. A filament of metal wire is fed into an extrusion nozzle head (3D printer extruder), which heats the material and turns the flow on and off. FDM is somewhat restricted in the variation of shapes that may be fabricated. Another technique fuses parts of the layer and then moves upward in the working area, adding another layer of granules and repeating the process until the piece has built up. This process uses the unfused media to support overhangs and thin walls in the part being produced, which reduces the need for temporary auxiliary supports for the piece.

Examples of a suitable method for manufacturing objects from the present magnesium alloys include powder bed fusion methods, which include several processes such as DMLS, SLS, SLM, MJF and EBM. Powder Bed Fusion processes can be used with an array of materials and their flexibility allows for geometrically complex structures. The starting material may be provided as powder. One example is direct metal laser sintering (DMLS). Another example is selective laser sintering (SLS). Another example, selective laser melting (SLM) does not use sintering for the fusion of powder granules but will completely melt the powder using a high-energy laser to create fully dense materials in a layer-wise method that has mechanical properties similar to those of conventional manufactured metals. Electron beam melting (EBM) is a similar type of additive manufacturing technology. EBM manufactures parts by melting metal powder layer by layer with an electron beam in a high vacuum. With laminated object manufacturing, thin layers are cut to shape and joined together.

Another example of a suitable method is powder-fed directed-energy deposition, a high-power laser is used to melt metal powder supplied to the focus of the laser beam. The powder fed directed energy process is similar to Selective Laser Sintering, but the metal powder is applied only where the material is being added to the part at that moment.

Additive manufacturing enables preparing complex or challenging objects, which may not be possible to prepare with conventional technologies. For example the inner parts of the object may contain specific structures, which cannot be formed for example by molding. It is possible to obtain objects which are light and contain specific structures, which may be needed in specific uses, such as in specific implants. It is also possible to prepare individualized object, for example medical devices, such as implants, designed for an individual, for example according to individual properties. For example it is possible to design and prepare a bone implant to treat a specific bone fracture or other condition. This may include imaging the patient, possibly creating a 3D model of the body part in need of treatment, such as specific bone(s), creating a 3D model of a medical device compatible with the body part in need of treatment, and preparing the medical device according to the 3D model by using additive manufacturing.

Injection molding may comprise any suitable injection molding method. Especially suitable injection molding methods include thixotropic molding, liquid metal molding and metal injection molding, preferably by using a binder.

Thixotropic molding, also called Thixomat or Thixomolding according to the developing company, is a precision magnesium casting method. Thixotropic molding refers to the thixotropic nature of magnesium alloys. When heated to just the right temperature-above the melting point of some alloy components, below that of others, the alloy turns into a slurry with solid and liquid portions. The slurry's thixotropic behavior enables the metal molding process to work very much like plastic injection molding. The process may be carried out as a single step process. Room temperature magnesium alloy chips are fed into a back end of a heated barrel through a volumetric feeder. The barrel is maintained under an argon atmosphere to prevent oxidation of the magnesium chips. A screw conveyor located inside the barrel feeds the magnesium chips forward as they are heated into the semi-solid temperature range. The material may be progressively heated in the machine barrel to about 40° C. below the liquidus of the alloy. The screw rotation provides the necessary shearing force to generate the globular structure needed for semi-solid casting. Once enough slurry has accumulated, the screw moves forward to inject the slurry into a steel die.

Processing temperatures up to 590° C. may be used. Compared to for example conventional die-casting, thixotropic molding enables obtaining higher density and elongation, smaller minimum wall thickness and better tolerance control.

In liquid metal molding small batches of magnesium alloy are melted in a vacuum chamber to avoid contamination from oxygen. The melted alloy is poured into the shot sleeve where a plunger pushes the material into a steel mold. The liquid metal molded part comes out of the mold to net shape, great precision, and with full physical properties. Secondary processes to remove the part from the runner and overflows are usually necessary.

Metal injection molding process involves combining fine metal powders with plastic binders which allow the metal to be injected into a mold using equipment similar to standard conventional plastic injection molding machines. After the part is molded and before the binders are removed, the part is referred to as a 'green part'. The next step is to remove the binders with solvents and/or thermal processes. The resultant metal part is sintered at temperatures great enough to bind the particles but not melt the metal.

The object may be a part of the implant, so the implant may comprise the object or a further object obtained from the initially formed object. The implant may also consist of the object or an object obtained from the initially formed object. For example the object may be further processed, for example mechanically and/or chemically. In mechanical processing the object may be processed to form one or more groove(s), aperture(s), thread(s) and the like forms. In chemical processing the object may be surface treated and/or coated with one or more coating(s), combined with one or more agent(s) or compound(s), reacted with one or more reagent(s), or combination(s) thereof. The object may be formed or included into a composite product. The surface treatment may refer to a treatment, which alters the surface of the alloy substrate, such as by chemical conversion, but does not necessarily add new material and/or result in a formation of a coating, at least a coating with a substantial thickness.

The forming may comprise forming the object into an implant. The implant may be any suitable implant, such as an orthopedic implant, for example a bone implant. The orthopedic implant may be in a suitable form, and it may be formulated or processed into the desired form. The implant may be or comprise any kind of implant used for surgical musculoskeletal applications. The implant may comprise a screw, a plate, a pin, a tack or a nail, such as intramedullary nail, preferably for the fixation of bone fractures and/or osteotomies to immobilize the bone fragments for healing; a suture anchor, a tack, a bolt, a clamp, a clip, a staple, a mesh, a scaffold, a cage, a Kirschner wire, a stent or other device preferably for bone-to-bone, soft tissue-to-bone, soft tissue-into-bone and/or soft tissue-to-soft tissue fixation; such as device used for supporting tissue or bone healing or regeneration; or cervical wedge or lumbar cage or plate, or a screw preferably for vertebral fusion and other operations in spinal surgery.

In one embodiment the implant is a screw. The screw may be a trauma screw or orthopedic surgical screw. The screw may be used in fixation of broken bones or in osteotomies in small bones in extremities, in long bones like femur, tibia, fibula, humerus, radius and ulna, in cranial bones, cranio maxillofacial bones, in spine or in bones in rib cage. The screw may be fully or partially threaded. A screw may include one or more screw thread(s). Threads may have constant or variable profile i.e. profile height and other dimensions may vary. Threading may have a constant or variable pitch. The screw may be fully threaded, or it may be partially threaded (lag). The screw may have a head, or it could be headless, such as a compression screw. The screw may be cannulated or non-cannulated. The screw may be used in weight (load) bearing or non-weight bearing applications. In orthopedics, weight bearing application refers to an injured body part a person puts weight through.

In one embodiment the implant is a plate. The plate may be used in fixation of broken bones or in osteotomies in small bones in extremities, in long bones like femur, tibia, fibula, humerus, radius and ulna, in cranial bones, cranio maxillofacial bones, in spine or in bones in rib cage. The plate may be fixed into the bone with special screws, tacks or pins. Design of the plate may be for example straight or curved, L-shape, X-shape, H-shape or any other planar geometrical shape. It may be bend in certain radius beforehand or during surgery for example by surgical pliers.

In one embodiment the implant is a tack. The tack may be used in various applications, where soft tissue is fixed to the bone in joint areas like knee, shoulder, hip, ankle, wrist or in hand or foot joints (fingers and toes). Soft tissue may be for example tendon, ligament, joint capsule or cartilage tissue.

In one embodiment the implant is a pin. The pin may be used in fixation of broken bones in either weight bearing or non-weight bearing applications. The pin surface may have longitudinal or transverse grooves or ridges in order to get better fixation torsional stability, higher pullout force and better liquid flow along the implant.

In one embodiment the implant is a nail. The nail may be used in fixation of broken bones in either weight bearing or non-weight bearing applications, as well as in soft tissue to bone fixations i.e. tendon, ligament, cartilage, joint capsule. The nail surface may have longitudinal or transverse grooves or ridges in order to get better fixation torsional stability, higher pullout force and better liquid flow along the implant.

In one embodiment the implant is an intramedullary nail. Intramedullary nail, also called as intramedullary device, intramedullary rod or inter-locking nail, is a metal rod which is designed to be forced into the medullary cavity of a bone, especially to treat fractures of long bones of the body.

In one embodiment the implant is a Kirschner wire. Kirschner wire, also called as K-wire or K-pin, is a sharpened, smooth wire or pin. A Kirschner wire may be provided in different sizes and is used to hold bone fragments together (pin fixation) or to provide an anchor for skeletal traction. A Kirschner wire typically has a diameter from 0.5 to 4 mm. It may be used in fixation of broken bones in typically non-weight bearing applications or to provide an anchor for skeletal traction. It may be drilled directly through the bones in its final implantation site and it may be bend during surgery. After getting the Kirschner wire in proper depth the excess of it may be cut with surgical pliers or saw. The Kirschner wire sharp point or it may have a flute or a thread with constant or variable height, for aiding K-wire to proceed through the bone while drilling. The Kirschner wire surface may have longitudinal or transverse grooves or ridges in order to get better fixation torsional stability, higher pullout force and better liquid flow along the implant.

In one embodiment the implant is a suture anchor. The suture anchor may be used to soft tissue, like tendons and ligaments fixation to the bone by means of one to three sutures each having two limbs. Suture anchor may be partially or fully threaded, barbed or expandable a screw or a rivet type. It has an eyelet, which may be recessed or prominent, hard or suture eyelet. Anchor may have a leading edge which may be either inserted into a pre drilled hole or directly screwed into bone.

In one embodiment the implant is a interference screw. The interference screw is a direct tendon-to-bone interference fixation device. It is a compression fixation device, which relies on the screw threads to engage and compress the graft to the bone in the drill hole for fixation. Interference screw may be used in fixation of soft tissue, bone-tendon-bone or bone-tendon grafts. Graft may be auto-, allo- or xeno-graft harvested from various locations of the body. Interference screw may be self-tapping or non-self-tapping.

In one embodiment the implant is a mesh or a scaffold. The mesh or the scaffold may be or comprise foam or fibrous structure. Fibrous structure may be weaved, knitted, braided or randomly oriented fibers. It may be 3-dimensional or flat sheet type of structure. It may be used in repairing defects in bony tissue or osteochondral tissue.

In one embodiment the implant is a wedge. The wedge may be used in opening wedge osteotomy for example in proximal tibia for correcting incorrect tibial plateau angle or in foot in flat foot reconstruction surgery.

In one embodiment the implant is a spinal cage. The spinal cage may be used for serving as a space holder between affected vertebrae. It allows bone to grow through it, eventually replacing it fusing two vertebrae together. Cage may have a solid, mesh type, hollow or perforated structure.

The implant may be elongated implant having a length: diameter ratio of 2 or more, such as 4 or more, 5 or more, 8 or more, or 10 or more. The implant may be an elongated bone fixation device, i.e. an orthopedic implant. The present materials and methods suit well for preparing elongated implants, and the properties of the material are suitable for such elongated objects.

In one embodiment the implant is an orthopedic implant, which is an elongated bone fixation device having a length: diameter ratio of 2 or more, such as 5 or more. The orthopedic implant may be selected from a screw, an intramedullary nail, a pin, a Kirschner wire and a staple.

The implant may consist of the magnesium alloy, especially when it is desired that the implant as a whole will degrade in the body. Alternately the implant may comprise a part obtained from the magnesium alloy, which may consist of the magnesium alloy, and further one or more other part(s), which may or may not be biodegradable. Examples of such implants include composite implants, such as fully biodegradable composite implants, which may consist of biodegradable materials.

Coatings and Surface Modifications

In order to modify the degradation of the final implants, to enhance their surface properties, or to add biologically active compounds therein, they can be further modified by an additional resorbable polymer coating layer with a process that may include co-extrusion, dip coating, electro spraying, injection molding, solution impregnation or any other known technique used in polymer, pharmaceutical, device or textile industry. The polymers may be one or more of those mentioned herein.

The object, the composite product, or the implant or the part thereof, may comprise a coating and/or a surface modification, i.e. a surface treatment, which is obtained by a suitable surface treatment method. Coatings for biomaterials, especially biodegradable magnesium, have the same requirements as the base materials themselves of being biocompatible and fully degradable. The latter point is particularly salient for understanding what occurs over the medical device life cycle. In the case of magnesium, coatings themselves cannot be perfect barriers to corrosion (which would be the goal of a coating system on a structural material). To allow an magnesium-based implant to biodegrade, the coatings must, at some stage, cease to be a corrosion barrier, although they may be required to provide an effective method to reduce the initial corrosion rate of the bare metal so the surrounding bone tissue (in the case of orthopedics) may start to form. Ideally, the coating would itself degrade gradually, helping to control the overall corrosion process while leaving no harmful traces. There are a large number of possible coating and/or surface modification technologies for magnesium biomaterials, including electrochemical plating, conversion coatings, anodizing, hydride coatings, ceramic coatings, vapor-phase processes, metal-metal coatings, plasma spray, plasma electrolytic oxidation (PEO), sputtering, chemical vapor deposition, atomic layer deposition (ALD), pulsed laser deposition, ion beam assisted deposition, solution, emulsion and suspension coatings, calcium phosphate (CaP) deposition achieved by various means and the well-known methods of electrodeposition and conversion coating.

A purpose of optional chemical coating in the present case may be to provide chemical or physical adhesion from magnesium or magnesium alloy to bioresorbable polymers and secondary corrosion resistance to magnesium or magnesium alloy and tertiary other properties e.g. antimicrobial or antibacterial properties.

Therefore in one embodiment the magnesium or the magnesium alloy is coated, either fully or partially, preferably with one or more substances disclosed herein and/or by using any of the methods disclosed herein.

Examples of substances which can be used for coating, but are not limited to, include organo-silanes, organo-titanates, organo-zirkonates, functionalized biodegradable polymers with capability to react with surface treated or untreated magnesium or its alloys, aluminum oxide, zinc oxide, metals e.g. zinc, gold, silver, copper, and nickel.

The chemical coating is optional and the chemical coating may comprise one or more layers of one or more substances in one layer or in different layers.

Electrochemical Plating

The plating process can be subdivided into two types: electroplating and electroless plating. In both cases a metal salt in solution is reduced to its metallic form on the surface of the workpiece. In electroplating the electrons for reduction are supplied from an external source. In electroless or chemical plating the reducing electrons are supplied by a chemical reducing agent in solution or, in the case of immersion plating, the substrate itself. Cu—Ni—Cr plating on magnesium or its alloys have been shown to have good corrosion resistance in interior and mild exterior environments, as magnesium and its alloys are also prone to galvanic corrosion because most other metals have a more noble electrochemical potential. Electrolytic contact with another metal can cause the formation of local corrosion cells on the surface leading to pitting. Therefore, the metal coating must be pore free otherwise the corrosion rate will increase. A minimum coating thickness of 50 um has been suggested to ensure pore-free coatings. Another advantage of electroless plating is that second phase particles such as carbides, diamonds or PTFE can be co-deposited during the plating process to improve the hardness, abrasive properties or lubricity of the bioresorbable glass fiber reinforced polymer matrix. To date zinc, gold, silver, copper, and nickel have been directly plated onto magnesium, and are used as under coatings or primer for subsequent process steps. Especially, zinc, silver and copper bring also antimicrobial properties to the chemical coating layer.

Plasma Electrolytic Oxidation

Plasma electrolytic oxidation (PEO), also known as micro-arc oxidation (MAO), is a surface coating technology that produces multiple ceramic layers on the surface of light metals and their alloys. The basic PEO process uses an electrolyte bath of a proprietary dilute aqueous solution, with additional reagents according to the desired surface coating properties. A high voltage, typically 200V or higher, is passed through the electrolyte and the high potentials generate plasma discharges on the substrate's surface, as shown in this video. The plasma in turn provides the ideal conditions of high temperature and pressure that forms a mainly crystalline oxide from the light metal substrate. The coating is a chemical conversion of the substrate metal into its oxide, and grows both inwards and outwards from the original metal surface.

Conversion Coatings

Conversion coatings are produced by chemical or electrochemical treatment of a metal surface to produce a superficial layer of substrate metal oxides, chromates, phosphates, silanes, titanates, zirconates or other compounds that are chemically bonded to the surface. Conversion coatings provide an adhesion by chemical bonding and/or affinity or physical entanglements polymer matrix and protect the substrate from corrosion by acting as an insulating barrier of low solubility between the metal surface and the environment and/or by containing corrosion inhibiting compounds. The use of alkoxy organo-silanes, organo-titanates, organo-zirconates i.e., those containing primary, secondary or tertiary alkoxy groups directly attached to silicon, titanium, zirconium as coupling agents for particulate material and polymeric resins is well known. Also use of fluorotitanates and zirconates are well known in coating of magnesium and magnesium alloys. Another chemical conversion process is to use a solution containing an organic additive and an organic acid, which has been shown to increase adhesion to polymers and passivate the metal surface. In such a process, after degreasing, the magnesium or its alloy is immersed in a solution containing sodium benzoate, sodium glucosate and an organic acid. The coatings produced were shown to have slightly better corrosion resistance than a chromate treated sample and environmentally and toxically safe. The morphology of the conversion coatings provides a good base for subsequent process steps which can further improve the adhesion and corrosion resistance of the treated magnesium part. In an alternative chemical coating process is a chemical treatment involving acid pickling in a hydroxy acetic acid solution followed by conversion coating with an organo functional silane compound. This process has been shown to maintain good adhesion and corrosion resistance in salt spray tests for coatings on magnesium alloys.

Hydride Coating

A technique for producing a magnesium hydride coating on magnesium and its alloys by electrochemical means has been developed as an alternative to Cr-based conversion coatings.

Anodizing

Anodizing is an electrolytic process for producing a thick, stable oxide film on metals and alloys. These coating layers may be used to improve polymer adhesion to the metal, as a key for dyeing or as a passivation treatment. The coatings have a thin barrier layer at the metal-coating interface followed by a layer that has a cellular structure. Each cell contains a pore whose size is determined by the type of electrolyte and its concentration, temperature, current density and applied voltage. Their size and density determine the extent and quality of sealing of the anodized coating.

Magoxid-coat process is an anodic plasma-chemical surface treatment that forms an oxide ceramic layer on magnesium materials. The plasma is discharged by an external power source in a slightly alkaline electrolyte near the surface of the workpiece, which acts as the anode of the system. The oxygen plasma generated causes partial short-term surface melting and ultimately the formation of an oxide-ceramic layer. The anodizing bath for this process is free of chloride and may contain inorganic anions such as phosphate, borate, silicate, aluminate or fluoride. The bath may also contain organic acids such as citrate, oxalate and acetate. A source of cations is also present and may be chosen from alkali ions, alkaline earth ions or aluminum ions. Finally, a stabilizer such as urea, hexamethylenediamine, hemethylenetetramine, glycol or glycerin is also added. The coating consists of three layers, a thin (about 100 nm) barrier layer at the metal surface followed by a low porosity oxide ceramic layer and finally a higher porosity ceramic layer. The final layer acts as a good base for polymer adhesion and impregnation treatments. Impregnation of the coating with particles of fluorine polymers has been shown to significantly improve the load bearing properties of the coatings while maintaining good adhesion and corrosion resistance. The coating has been shown to consist of mainly $MgAl_2O_4$. This process is capable of producing uniform coatings even on edges and cavities.

Gas-Phase Deposition Processes

All the processes discussed thus far have been wet chemical surface treatments. Adhesive and protective coatings can also be produced from the gas phase. These are typically metallic or metal oxide coatings but can include organic coatings such as thermal spray polymer coatings and diamond like coatings. Thermal spray coatings are gas-phase deposition processes where the coating material, which can be metal, ceramic, cermet or polymeric is fed to a torch or gun where it is heated to above or near its melting point. The resulting droplets are accelerated in a gas stream onto the substrate and the droplets flow into thin lamellar particles and adhere to the surface. A number of coating techniques fall under this umbrella including flame spraying, wire spraying, detonation gun deposition, plasma spray and high velocity oxyfuel. Some of the advantages of this technique include the ability to create a coating of virtually any material that melts without decomposing, minimal substrate heating during deposition and the ability to strip and recoat worn or damaged coatings without changing the properties or dimensions of the part. As with most surface treatments, in order to ensure adequate adhesion, the substrate must be properly prepared. The substrate must be both cleaned and roughened prior to the application of the thermal spray coating. Chemical vapor deposition (CVD) is a vacuum deposition method used to produce high quality, high-performance, solid materials. The process is often used to produce thin films. CVD to deposit materials in various forms, including: monocrystalline, polycrystalline, amorphous, and epitaxial. These materials include: silicon (dioxide, carbide, nitride, oxynitride), carbon (fiber, nanofibers, nanotubes, diamond and graphene), fluorocarbons, filaments, tungsten, titanium nitride. Chemical vapor deposition (CVD) can be defined as the deposition of a solid on a heated surface via a chemical reaction from the gas phase. Advantages of this technique include deposition of refractory materials well below their melting points, achievement of near theoretical density, control over grain size and orientation, processing at atmospheric pressure and good adhesion. This process is not restricted to line of sight like most physical vapor deposition (PVD) processes so deep recesses, high aspect ratio holes and complex shapes can be coated. A plasma-assisted CVD technique has been successfully used to deposit TiCN and ZrCN layers on magnesium alloys. A process for producing a protective film on magnesium containing substrates may involve CVD of an intermediate aluminum layer, followed by a metallic oxide layer of titanium oxide, aluminum oxide, zirconium oxide, chromium oxide or silicon oxide. Diamond like carbon films can be produced using a number of different processes such as PVD, CVD and ion implantation. Diamond-like carbon films on magnesium alloys with good lubricity, corrosion resistance, adhesion and smoothness have been produced using a CVD process. PVD involves the deposition of atoms or molecules from the vapor phase onto a substrate. This process includes vacuum deposition, sputter deposition, ion plating, pulsed-laser deposition and diffusion coatings. PVD-PLD may be used to coat magnesium substrates with titanium or titanium alloy material. A focused laser beam is used to heat and vaporize the titanium or titanium alloy target. The vapor is deposited on the magnesium or magnesium alloy substrate to form a thin film.

Atomic layer deposition (ALD) is a thin-film deposition technique based on the sequential use of a gas phase chemical process; it is a subclass of chemical vapor deposition. The majority of ALD reactions use two chemicals called precursors. These precursors react with the surface of a material one at a time in a sequential, self-limiting, manner. Through the repeated exposure to separate precursors, a thin film is slowly deposited. ALD is a suitable method to produce thin coatings based on metal oxides (e.g. $Al_2O_3$ and ZnO) and nitrates (e.g. SiN).

Organic finishing is typically used in the final stages of a coating process. These coatings can be applied to enhance adhesion, corrosion resistance, abrasion and wear properties. An appropriate pretreatment process is required in order to produce coatings with superior adhesion, corrosion resistance and appearance. Magnesium surfaces must be free of surface contamination, smut and loose silicates, oxides and intermetallic compounds. Cleaning processes for magnesium can involve mechanical pretreatment, solvent cleaning or alkaline cleaning. Cleaning is typically followed by a pickling or an etching step coupled with a chemical treatment, such as conversion coating or anodizing. These treatments roughen and chemically modify the surface so that the organic coating will have good adhesion to the surface. Another technique for treating magnesium surfaces prior to the application of an organic coating involves exposing the material to an aqueous solution containing an organic compound after appropriate cleaning and pickling procedures. The compound must have a particular structure XYZ, where X and Z are both polar functional groups and Y is a straight chain structure with 2-50 carbon atoms. Some examples of these include I-phosphonic acid-12-(N-ethylamino)dodecane, I-phosphonic acid-12-hydroxy-dodecane, p-xylylene diphosphonic acid and 1,12-dodecane diphosphonic acid. These compounds react with the hydroxide groups on the magnesium surface through the acid groups to form a chemical bond. There is also a reaction between the remaining functional groups and the subsequent organic coating. These coatings are to significantly improve polymer adhesion and to inhibit corrosion. Organic coating systems can include a variety of different processes that make use of biodegradable organic polymers, such as painting, powder coating, E-coating (cathodic epoxy electrocoating) and the application of lacquers, enamels and varnishes. Powder coatings can be applied in a number of ways including electrostatic powder spraying, fluidized bed or flame spraying of thermoplastic powders. Flame spraying has been used in the application of ethylene acrylic acid (EAA) copolymers on a variety of substrates. In this process the plastic powder is propelled through a flame that heats and melts the polymer and the surface so that the coating particles coalesce and flow into a continuous coating. The EAA polymers have been shown to have excellent adhesion to metals due to the acrylic acid functional groups, which promote adhesion by hydrogen and ionomeric bonding to the substrate. These systems can be based on a variety of biodegradable or water soluble coating resins such as polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/e-caprolactone copolymers, L-lactide/DL-lactide copolymers, glycollide/L-lactide copolymers (PGA/PLLA), polylactide-co-glycolide; terpolymers of PLA, such as lactide/glycolide/trimethylene carbonate terpolymers, lactide/glycollide/e-caprolactone terpolymers, PLA/polyethylene oxide copolymers; polydepsipeptides; unsymmetrically 3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone—poly-s-capralactone, Polytyrosines and its copolymers; polyacrylamides, poly(e-caprolactone-DL-lactide) copolymers; methylmethacrylate-N-vinylpyrrolidone copolymers; Polyvinylpyrrolidone and its copolymers; polyesteramides; polyacrylic acids, polybutylene succinate, polyoxazolines, Polyethylene glygols, polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanoic acids; polycarbonates; polyorthoesters; polyphosphates; Polyphosphazenes; poly(ester anhydrides); biodegradable liquid crystal polymers; Xanthan Gum; Pectins; Dextran; Carrageenan; Guar Gum, Cellulose Ethers; Glucomannan; Sodium CMC; HPC; HPMC; and mixtures thereof; and natural polymers, such as sugars; Starch or Starch Based Derivatives, cellulose and cellulose derivatives, polysaccharides, collagen, chitin, chitosan, fibrin, hyaluronic acid, polypeptides and proteins. Mixtures and copolymers of any of the above-mentioned polymers and their various forms may also be used. Traditionally, organic coatings have been solvent based which poses a significant environmental concern with their use. However alternative processes that eliminate this problem are available. Some of these include powder coatings, the use of compliance solvents and waterborne solvents. The primary function of organic coatings is to act as an interface between the metal substrate and polymer matrix. It is important that these coatings provide functional groups and/or chemical affinity and/or physical entanglements to react to form a chemical bond or physical bond with polymer matrix. In manufacturing methods where physical damage is likely to occur it is also important that the coating have self-healing characteristics. This can be accomplished by the presence of corrosion inhibiting pigments or additives in the coating or using a sacrificial anodic compound in the coating. For an organic coating to act as an effective adhesive and protection, it must be uniform and well-adhered to the magnesium or magnesium alloy or primer, a multiple layer coating system may be used which is consisting of a topcoat, that is typically the most hydrophobic and UV resistant coating, and primer and mid-coats that have high crosslink density and wet adhesion to the magnesium and each other. With a multiple layer system, it is unlikely that defect areas will overlap, this ensures that the substrate is completely coated with organic material. These coatings may be also elastomeric to absorb and dissipate impact energy. The organic coating may also include additives e.g. an antimicrobial agent such as halogen substituted silanes.

Sol-Gel Process

Synthesis of gels or glasses by the sol-gel process involves the hydrolysis and condensation polymerization of metal alkoxides, alkoxy-silanes, -titanates, -zirconates and/or phosphates. This process can be used to produce polymeric networks of inorganic-organic composite materials. It is possible to form adherent, uniform coatings on metal surfaces by the addition of components, to the reaction mixture, that are reactive with the surface that is to be coated. This process can produce corrosion-protective coatings on magnesium and magnesium alloys by a simple wet coating technique through the formation of a stable tailored interface. The coatings are transparent with excellent adhesion, scratch and abrasion resistance, and corrosion protection. One approach is to produce bioglass coating to the magnesium and its alloys by Sol-gel process, one example of such a sol-gel bioglass composition is 58S (60 mol % $SiO_2$, 36 mol % CaO, 4 mol % $P_2O_5$).

Coatings for biomaterials, especially bioresorbable magnesium and its alloys, have the same requirements as the base materials themselves of being biocompatible and fully degradable. The latter point is particularly salient for understanding what occurs over the implant life cycle. In the case of magnesium, coatings themselves cannot be perfect barriers to corrosion (which would be the goal of a coating system on a structural non-degradable material). To allow an hybrid composite implant to biodegrade, the coatings must, at some stage, cease to be a adhesion interface and corrosion barrier, although they are required to provide an effective method to provide good adhesive interface to polymer and reduce the initial corrosion rate of the bare metal so the surrounding bone tissue (in the case of orthopedics) may start to form. Ideally, the coating would itself degrade gradually, helping to control the overall corrosion process while leaving no harmful traces.

The chemical coatings and/or modifications must be biocompatible and non-toxic and display a controlled biodegradation rate.

The object, the composite product, or the implant, may comprise bioresorbable and/or bioactive glass. Bioresorbable and bioactive glasses have a capability of reacting with physiological fluids forming tenacious bonds to bone through the formation of bone-like hydroxyapatite layers leading to effective biological interaction and fixation of bone tissue with the material surface. Moreover, in the case of silicate and phosphate bioactive glasses reactions on the material surface induce the release and exchange of critical concentrations of soluble Ca, P and Na ions, which can lead to favorable intracellular and extracellular responses promoting rapid bone formation. Bioresorbable glass compositions may be provided containing no sodium or additional elements incorporated in the silicate or phosphate network such as fluorine, magnesium, strontium, iron, silver, boron, potassium, zinc, copper, barium, lithium or combinations thereof. Fabrication techniques for bioactive glasses or glass fibers include both traditional melting methods and sol-gel techniques. The typical feature common to all bioactive glasses, being melt or sol-gel derived, is the ability to interact with living tissue, in particular forming strong bonds to bone (and in some cases soft tissue, a property commonly termed bioreactivity or bioactivity, as mentioned above. For establishing bond with bone, such a biologically active apatite, a surface layer must form at the material/bone interface. Thus, one basis of the bone bonding property of bioactive glasses is the chemical reactivity in physiological body fluids (in vitro and in vivo), which may result in the formation of a hydroxycarbonate apatite (HCA) layer to which bone can bond. Briefly, the processes on the glass surface are characterized by ion leaching/exchange, dissolution of the glass network and precipitation and growth of a calcium-deficient carbonated apatite (HCA) surface layer, whereas cellular reactions include colonization, proliferation and differentiation of relevant (bone) cells.

The bioactive glasses presented in previous exhibit several advantages in comparison to other bioactive ceramics, e.g. sintered hydroxyapatite, in tissue engineering applications. Polymer/bioceramic composite materials represent a convenient alternative due to the possibility to tailor their various properties (e.g., mechanical and structural behavior, degradation kinetics and degree of bioactivity). Composites made of polymers and bioceramics may combine the advantages of their singular components. Polymers exhibit generally high ductility, toughness, favorable formability as well as processability and plasticity. The glass or glass-ceramic phase adds stiffness and mechanical strength to the composite. In particular, composites based on biodegradable polymers may be useful as bone tissue engineering materials because this particular combination does not require a revision surgery for their removal as newly formed bone gradually substitutes the implanted material during degradation.

Composite Materials and Implants

In one embodiment the implant is in a form of a composite with one or more polymer(s), glass fiber(s), bioglass and/or ceramic material(s) such as hydroxyapatite, tricalcium phosphate, calcium carbonate, calcium sulphate, which may all be biodegradable, and/or is doped with silicone, magnesium etc. The implant may comprise the composite or it may consist of the composite.

The magnesium alloy is provided as a separate part having reinforcing properties, such as a core, for example a rod, a plate, a tube or fibers or other reinforcing shape, such as any of the shapes or forms disclosed herein, which may represent the part of an implant.

Preferably the magnesium alloy is provided as a self-standing or self-supporting form or shape. The magnesium alloy may be formed first and then combined with the other materials. Magnesium alloy as a coating, such as a coating deposited or otherwise formed on other materials, for example by sputtering, is excluded.

The implant may comprise or be based on composite material comprising the magnesium alloy, which composite material may be in a form of a composite product. The composite material may be any type of applicable composite material. The process for manufacturing the composite material may be a continuous process or a batch process. The composite material may be a hybrid composite material comprising more than two types of materials.

In composite materials the main input from magnesium alloys comes from stiffness and flexural modulus. Other components of the composite may include for example glass, such as bioresorbable glass, which may be included to regulate the strength, corrosion properties and hydrogel gas evolution, and/or polymer, such as one or more type of polymer, such as plastic polymer.

Hybrid Composite Material

The composite material may be hybrid composite material, which may comprise three or more materials. The (hybrid) composite material may comprise the present biodegradable magnesium alloys combined or embedded with bioresorbable glass fiber reinforced polymer matrix. The biodegradable magnesium alloy therefore forms a part of the composite implant. It may further comprise a coating on the surface of the magnesium alloy, preferably to act as an adhesion layer to bioresorbable glass fiber reinforced polymer matrix and/or to act as further layer to slow down hydrogen gas evolution. It may also act as a hydrogen trap, which prevents hydrogen release from the structure, and/or it may keep corrosion products on the magnesium alloy's surface forming corrosion inhibiting layer.

The present hybrid composite materials are suitable for application requiring certain mechanical properties, such as resistance for compression and/or tension.

The present hybrid composite materials are suitable for several medical treatment methods and application, especially ones involving bones and/or implanting. The materials exhibit similar mechanical properties as the bones to be treated. For example the composite materials have similar compression strength as cortical bones, unlike commonly used materials such as titanium-based materials.

The present hybrid composite materials also exhibit efficient bioactivity, such as osteoinductive properties. This is important in several applications, such as in cases wherein regeneration of bone is desired, for example when medical products are inserted in spine.

The present composite materials are also fully biodegradable and bioresorbable, so that all the materials used in the composite will be substantially degraded in body, and the degradation products will be metabolized in a safe manner, i.e. bioresorbed. There is no need to remove the biodegradable products, such as implants, from the body, and therefore unnecessary surgeries or other medical treatments such as anaesthesia can be avoided, which is especially important with high risk patient group, such as paediatric or geriatric patients or patients with poor condition.

The composite materials are useful as structural fixation for load-bearing purposes, exhibiting improved mechanical properties as a result of hybrid composite structure, unlike the composites of prior art. Indeed, the disadvantages of the prior art are overcome or at least minimized by the solutions of the present application, which provides hybrid composite materials wherein the magnesium alloy is combined or embedded with bioresorbable glass fiber polymer matrix.

The hybrid composite material can minimize or even eliminate drawbacks of the prior art materials, i.e. the composite retains its strength and modulus in vivo for example for a time period sufficient for bone fracture healing. Indeed, high strength and flexural modulus matched with cortical bone with good strength retention in vivo conditions can be achieved through combining two bioresorbable reinforcement, magnesium/magnesium alloy and glass fiber into bioresorbable polymer matrix. Mechanical strength as used here includes bending strength, torsion strength, impact strength, compressive strength and tensile strength.

The hybrid composite material is malleable i.e. surgeon can shape the implant by bending it according to the bone's anatomy and shape before inserting it. Due to the hybrid composite materials' metallic, plastic nature the new shape will stay unchanged during the healing period. The malleability may be based mainly or substantially on the magnesium alloy. The magnesium alloy is provided as a self-supporting form, such as an self-supporting object. Self-supporting refers to such form which is rigid enough to be malleable and to provide reinforcing properties and/or mechanical strength for implant uses, such as when inserted into a bone. Self-supporting object may be self-standing, and can exist as such, for example a self-supporting object may be provided, handled and processed.

The reinforcing form of the magnesium alloy may therefore act or be present, act as and/or form one or more core(s), and it is embedded, such as mixed, covered or coated, with the bioresorbable glass fibers and the bioresorbable polymer. When the magnesium alloy is present or provided as a tube it may be desired not to fill the aperture of the tube with any substance but it may be left unfilled to allow use of suitable handling during applying and/or removing the product into or from a body. In other words, the magnesium alloy may form a core of the hybrid composite material, which is embedded in the bioresorbable glass fiber reinforced polymer matrix. Therefore the bioresorbable glass fiber reinforced polymer matrix surrounds the magnesium alloy core, either fully or partially.

The present biodegradable magnesium alloy is provided in a reinforcing form, which means that it is present as a reinforcement, which can provide mechanical support. Reinforcing form may refer to self-supporting, especially to material which is provided as self-supporting, for example it is not provided and/or present as a coating on a different material. The magnesium alloy may be in a form of one or more of a rod, a plate, a tube or fibers or other reinforcing shape, in general a self-supporting shape, which may be a physical form which brings a reinforcing effect to the hybrid composite and may be embedded by bioresorbable fiber reinforced polymer matrix.

According to examples, the amount of the magnesium alloy in the hybrid composite or the hybrid implant may be 1-99 weight-%, preferably 10-90 weight-%, more preferably 20-80 weight-%, and most preferably 30-70 weight-% of the total weight of the hybrid composite material or the hybrid implant.

Although the lower strength of Mg compared to Ti may be beneficial with respect to stress shielding, it also means that there may be a greater chance of failure in high load applications, such as the spine where compressive loads during certain activities may exceed 3500 N. It is vital to ensure that any implant is designed to sustain its load without deformation. However, this aspect is even more crucial when considering degradable materials, as an appropriate mechanical support is required throughout the entire bioresorption and bone remodeling process.

The bioresorbable glass fibers and bioresorbable polymer may be first combined and subsequently combined with the reinforcing form of magnesium alloy. The bioresorbable glass fibers and bioresorbable polymer may be provided as a ready-made product, i.e. a glass-fiber-polymer composite, for example as a tape, a filament, a yarn, a machined object and/or as a moldable composite material. The glass-fiber-polymer composite may be further heated, pressed and/or otherwise processed and/or reacted to form it into a desired form, i.e. combined with the magnesium alloy. For example the glass-fiber-polymer composite may be heated before and/or during applying onto the reinforcing form of magnesium alloy. The glass-fiber-polymer composite is preferably heated to obtain a melt of the polymer. The polymer should be melted in such degree that it becomes mouldable. After the glass-fiber-polymer composite is applied, it will be cooled or let to cool to solidify the melt.

It is also possible to have a different combination order, for example the reinforcing form of magnesium alloy may be first combined with the bioresorbable polymer and subsequently combined with the bioresorbable glass fibers.

One embodiment provides a fully biodegradable implant, such as an orthopedic implant, comprising the biodegradable magnesium alloy as a self-supporting core embedded in bioresorbable glass fiber reinforced polymer matrix.

In one embodiment the method comprises
  combining the bioresorbable glass fibers and the bioresorbable polymer to obtain bioresorbable glass fibers in a bioresorbable polymer matrix, and
  combining the bioresorbable glass fibers in a bioresorbable polymer matrix with the reinforcing form of magnesium alloy to form the biodegradable composite material.

In one embodiment the method comprises
  combining the reinforcing form of magnesium alloy and the bioresorbable polymer to obtain reinforcing form of magnesium alloy in a bioresorbable polymer matrix, and
  combining the reinforcing form of magnesium alloy in a bioresorbable polymer matrix with the bioresorbable glass fibers to form the biodegradable composite material.

Any suitable combining methods or combinations thereof may be used, such as one or more selected from applying, compressing, melting, laminating and polymerizing. In most cases it is necessary to provide the polymer(s) or precursor(s) thereof in a mouldable state, such as molten or flowable state, so that the polymer may form a matrix around the glass fibers and/or the magnesium alloy.

When combining the ingredients, in some methods it is necessary to obtain or form a melt, more particularly a melt of the bioresorbable polymer. This can be achieved by using increased temperature, such as a temperature at the melting point of the bioresorbable polymer or higher. The bioresorbable polymer may be or comprise thermoplastic polymer. The melt polymer is then combined and/or mixed with the glass fibers and/or the magnesium alloy.

In such way it is possible to combine the polymer with the other ingredient(s), so that a mixture is formed, which may be called a composite material, wherein the polymer is present as a matrix. It is possible to obtain the polymer or polymer matrix by providing a precursor of the polymer or polymer matrix, such as monomers, oligomers and/or polymers, which are formed into the desired polymer by using suitable reaction, such as polymerization reaction. A polymerization initiator may be provided, such as a chemical initiator, (UV) light, other radiation and/or heat.

Pressure may be applied during combining, such as by compressing with a suitable device, which pressure may cause the polymer(s) or precursor(s) therefore to become mouldable. Heat may be also used, which may be external heat and/or heat caused by applying the pressure.

Figure 10:
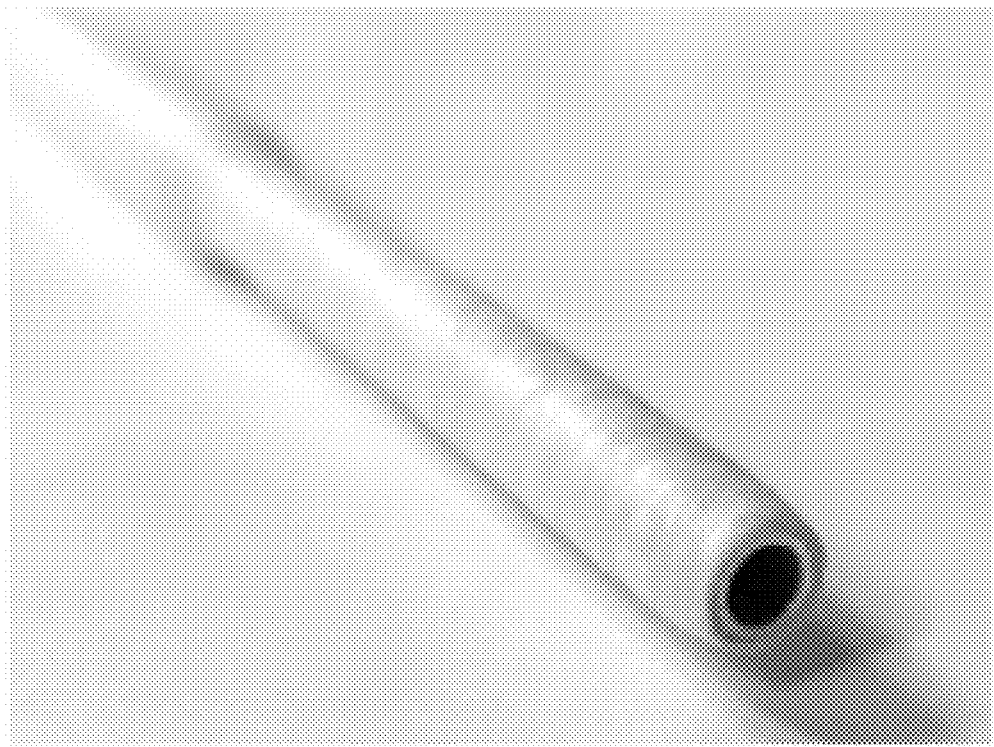
FIG. 10 shows an example of the present hybrid composite implant.

When the reinforcing form of magnesium alloy is provided as a core or the like structure, the bioresorbable glass fibers and the bioresorbable polymer may be provided to cover this self-supporting structure, for example by winding, such as by filament winding or tape winding, which may be thermoplastic winding, for example wherein glass fiber-polymer tape is wound onto a magnesium core, such as shown in FIG. 10, or by providing a melt of the bioresorbable glass fibers in a bioresorbable polymer matrix onto the reinforcing form of magnesium alloy by using any suitable method such as by kneading, by extruding including coextrusion and thermoplastic pultrusion, by injection moulding or by any other devices and methods disclosed herein. Magnesium part and/or glass fiber in polymer matrix part may be provided as objects machined to fit each other, and then applied to combine and form a composite structure. For example a rod of magnesium alloy may be applied into an aperture in a glass-fiber-polymer tube or other suitable structure adapted to receive said rod. The fitting shall be preferably a tight fitting, such as a fitting requiring compression during applying so that the rod is forced into the aperture, thus resulting in a compressive contact between the two objects.

Magnesium alloy may be first processed and/or machined into a desired form for combining with the other ingredients by using any suitable processing or machining devices, such as by mechanical machining, laser machining, pressing, water jet processing, additive manufacturing, such as including providing the biodegradable magnesium alloy as powder, granules or as a wire, or injection molding, such as by thixotropic molding, liquid metal molding or metal injection molding, or by combinations thereof. After this processing and/or machining a suitable form, such as a rod, a plate, a tube or fibers or other physical form or shape can be obtained.

The bioresorbable glass fibers may be provided in continuous form and/or in discontinuous form. Also the reinforcing form of magnesium alloy may be provided in continuous form and/or in discontinuous form.

According to one example the hybrid composite material comprises two or more types of resorbable and biocompatible glasses or glass fibers, each type having a different composition, resorption rate and/or bioactivity. The glasses, or types of glasses, may be called as a first glass, a second glass and optionally a third or further glass(es) by running number. A second type of glass can be for example a glass having higher bioactivity and resorption rate. In the case of a faster resorption rate and a higher bioactivity, the main function is not the reinforcement of the composite, but instead to be a more osteoconductive or antimicrobial material, which means that it promotes and facilitates bone healing, in the form of granules, fibers and/or powder, such as for example BonAlive® S53P4 glass. The different types of glasses may be for example different types selected from silica, phosphate, boron and magnesium based bioresorbable glasses.

The composite material may also comprise two or more types of bioresorbable polymers, two or more types of chemical coatings or partial coating/coatings, coatings with pattern or coatings with the variable thickness, which provide design specific optimized/programmed corrosion rate or adhesion behavior. Moreover, the composite material may also comprise the glass in the form of two or more groups of fibers having different median diameters.

The composite materials disclosed herein may be called as hybrid composite materials. The term hybrid composite as is used in this description refers materials that are the result of a combination of several phases where at least two reinforcement elements are integrated into a matrix to improve the composite's properties i.e. hybrid composites can be defined as the materials that comprise or consist of two or more types of reinforcements embedded in a single polymer matrix. The morphology, nature, and orientation of components are significantly affecting the manner that the composite reacts against external loads. In fact, the properties of the composite are closely linked to its internal structures, which are governed by the characteristic properties of the constituent elements of the hybrid composite. The mechanical properties of hybrid composites consist of n (n>2) jointly working phases, which are very important. However, the mechanical behavior of hybrid composites depends not only on the character of a matrix and reinforcements but also on properties of the interface between these components and the matrix, which must be taken into consideration. Since hybrid composites use more than one kind of reinforcement in the same matrix; hence, the idea is to get the synergistic effect of the properties of reinforcements on the overall properties of composites. With hybrid composites it may be possible to have greater control of the properties, achieving a more favorable balance between the advantages and disadvantages inherent in any composite material. Furthermore, the positive hybrid effect could be noticed in such materials as the load could still be bridged to the surrounding high elongation reinforcement (the magnesium alloy) upon the fracture of the reinforcements having low elongation (glass fiber), thus resulting in enhanced mechanical properties of the composites.

In fact, hybrid composites can be considered as the weighted sum of the individual constituents in which a balance of advantage and disadvantages of the constituents shall be achieved. It is identified that the advantages of one reinforcement could complement the disadvantages of another reinforcement through the hybridization like according to this disclosure magnesium alloys with higher stiffness and flexural modulus complements the bioresorbable glass fiber reinforced polymer matrix stiffness and flexural modulus. Similarly, bioresorbable glass fiber reinforced polymer matrix complements the strength properties of magnesium alloy. Therefore, hybrid composite made from magnesium alloy and bioresorbable glass fiber reinforced matrix yields optimal strength, stiffness and modulus, what is required from load-bearing implant or structural material.

The properties of a hybrid composite can be influenced by the orientation of the reinforcements, reinforcement content and length, layering patterns of the two reinforcements, their intermingling capacities, reinforcement-to-matrix interface, and also the failure strain of single reinforcements.

According to one embodiment the hybrid composite has a flexural strength of 200-1500 MPa, more preferably 300-800 MPa or 300-500 MPa, and most preferably 400-500 MPa measured by ISO 178:2019 or ASTM D790-17.

According to another embodiment the hybrid composite has a flexural modulus of 20-40 GPa, more preferably 25-35 GPa and most preferably about 30 GPa measured by ISO 178:2019 or ASTM D790-17.

According to another embodiment the hybrid composite has a shear strength of 4000-5000 N, more preferably 4200-4800 N, measured by BS 2782-3 method 340A-B (rate 10 mm/min).

The hybrid composite may retain at least 60% of its mechanical properties in physiological conditions (in vitro, temperature 37° C.) at least for 3 months, preferably for 4-5 months and most preferably for 6 months measured by ISO 178:2019 or ASTM D790-17.

The present application also relates to the use of the hybrid composite material in the preparation or manufacture of a medical device. The present application also relates to a medical device comprising the hybrid composite material as explained herein. The medical device may be for example an implant. The medical devices manufactured from the composite, having high strength, modulus just above cortical bone and retention of those properties in vivo are useful in manufacturing of e.g. bone fracture fixation devices, because aforementioned properties yield the same design freedom and the usability as current inert biometals, such as titanium and its alloys under hydrolytic conditions.

The medical device may be any kind of implant used within the body or a device for supporting the tissue or bone healing and/or regeneration.

An implant according to the present context may comprise any kind of implant, more particularly a (fully) bioresorbable implant, which may be used for surgical musculoskeletal applications, such as a screw, a plate, a pin, a tack or a nail, for the fixation of bone fractures and/or osteotomies to immobilize the bone fragments for healing; a suture anchor, a tack, a screw, a bolt, a nail, a clamp, a stent and other devices for bone-to-bone, soft tissue-to-bone, soft tissue-into-bone and soft tissue-to-soft tissue fixation; devices used for supporting tissue or bone healing or regeneration; or cervical wedges and lumbar cages and plates and screws for vertebral fusion and other operations in spinal surgery.

In some further examples the implant comprises a nail, such as intramedullary nail, for the fixation of bone fractures and/or osteotomies to immobilize the bone fragments for healing, a clip, a staple, a mesh, a scaffold, a cage, or a Kirschner wire.

The present hybrid composite materials are especially suitable for large or massive implants and the like medical devices, such as plates, nails or screws, or to any other implants and medical devices exposed to compression, tension and/or torsion forces. Such nails or screws may have a length of the least 10 cm, at least 15 cm or at least 20 cm. The materials can provide desired mechanical properties to such products, such as bending strength, torsion strength, impact strength, compressive strength and tensile strength.

In one embodiment the bioresorbable implant comprises or is an intramedullary nail. Intramedullary nail, also called as intramedullary device, intramedullary rod or inter-locking nail, is conventionally a metal rod which is designed to be forced into the medullary cavity of a bone, especially to treat fractures of long bones of the body. The present hybrid composite materials are especially suitable for preparing intramedullary nails, which are large structures usually made of titanium which therefore needs removing from a body. This may be a laborious and high-risk operation requiring anaesthesia, surgical methods and use of force, which may lead to complications, further injuries or other non-desired effects such as discussed herein. With the present hybrid materials it is possible to provide biodegradable intramedullary nails, which do not need removing but which exhibit very good mechanical properties required in such large nails, such as high strength, stiffness and modulus. With the present manufacturing methods it is possible to easily obtain such massive nails with desired size and properties. As the product is biodegradable, it does not require removing so many of the drawbacks of the conventional intramedullary nails can be avoided.

In one embodiment the bioresorbable implant comprises or is a scaffold or a cage, such as spinal cage. A spinal cage, also called as an interbody cage or interbody fusion cage, is a prosthesis used in spinal fusion procedures to maintain foraminal height and decompression. They may be for example cylindrical or square-shaped, and may be threaded. Such implants are inserted when the space between the spinal discs is distracted, such that the implant, when threaded, is compressed like a screw. FIG. 3 shows an example of a spinal cage 10 comprising a magnesium alloy honeycomb structure 14, which may be filled with osteoconductive or osteoinductive material, such as polymer composite material. The outside layer 12 is formed of glass-fiber-polymer layer surrounding and supporting the magnesium alloy structure. As the spinal cage 10 is open including two large apertures and honeycomb structure and is subjected to compressing forces during use, it is important that the whole structure can tolerate these mechanical forces without deforming. In general, the present hybrid materials are suitable for supporting different kind of cellular or porous structures, such as said honeycomb structures or other structures containing pores, voids or apertures. The present materials may comprise such cellular portions or other porous portions, such as cellular portions comprising or consisting of the magnesium alloy. Examples of such products include the cages, scaffolds or other applicable products disclosed herein.

The present hybrid composite materials are especially suitable for such scaffolds and cages, which must tolerate high pressure load or stress. Conventional biodegradable materials are not very durable in such use, especially polymer-based materials tend to compression creep and flatten. In the present hybrid materials the non-creeping glass fiber can hold the implants together, and the magnesium provides compression strength. The glass fiber may be wound or otherwise placed around the reinforcing form of the magnesium alloy, so the spreading of the magnesium material can be suppressed.

The basic premise of a spinal fusion is the creation of a bone "bridge" that connects strong and healthy bone above the weakened spinal segment with strong and healthy bone below it.

Long-term spinal stability is best achieved with good fusion of the bones. The process of bone fusion takes several months or up to a year or more for patients with fusions that extend over several spinal segments. Current metallic cages e.g. titanium cages, which are currently the golden standard in spinal fusion, are often associated with excessive rigidity that may increase postoperative complications such as stress shielding, device-related osteopenia, and subsidence. Although superior in mechanical strength, metallic cages are non-bioactive and often fail to effectively transfer loads to stimulate bony tissue remodeling. Radiopaque metallic cages also interfere with visualization of bony fusion at the graft site during postoperative follow-up, making it difficult to determine the progress of bony healing. The present biodegradable cages are especially suitable in spinal procedures involving interbody fusion to resolve complications associated with the use of nondegradable cages, such as stress shielding and long-term foreign body reaction. In prior art the relatively weak initial material strength and low creep resistance of biodegradable cages compared to permanent materials and subsequent decrease of strength due to degradation has been problematic and has not yielded favorable clinical outcome. The bioactivity of the present biodegradable hybrid composite enables fast bone-bonding of the cage to vertebrae and prevents implant migration and displacement, and moreover stimulates bony tissue remodeling over and through the hybrid composite implant from vertebra to vertebra i.e. spinal fusion. The mechanical properties of hybrid composite cage are isoelastic with cortical bone as shown in example 6 and not causing stress shielding but stronger than current biopolymer cages and therefore enable adequate stability to spinal fusion. Additionally the hybrid composites are MRI safe and they do not interfere with post-operative visualization.

In one embodiment the implant comprises or is a screw. The screw may be a trauma screw or orthopedic surgical screw. A screw usually includes one or more screw thread(s).

Kirschner wire, also called as K-wire or K-pin, is a sharpened, smooth wire or pin. They may be provided in different sizes and are used to hold bone fragments together (pin fixation) or to provide an anchor for skeletal traction.

The hybrid composite material may also be used as a porous tissue engineering scaffold. The scaffold, or the composite material or a medical device containing thereof, may have a porosity degree in the range of 40-95%, such as in the range of 40-60% 40-90% 60-90% or 60-80%, preferably at least 80%, and more preferably at least 90%.

Bioresorbable Glass Fiber Reinforced Polymer Matrix

The present application provides a hybrid composite material comprising magnesium or magnesium alloy included, such as embedded, in a discontinuous or continuous bioresorbable glass fiber reinforced polymer matrix. The composite material disclosed herein preferably comprises free fiber orientation in a one or more successive layers, preferably at least glass fibers, wherein the layer comprises a bioresorbable polymer matrix and a bioresorbable reinforcing fiber or fiber bundle.

The term "free fiber orientation" refers to unrestricted choice of fiber orientation of the bioresorbable reinforcing fiber or fiber bundle of the bioresorbable glass fiber reinforced polymer matrix when designing the desired fiber orientation of the orthopedic implant. The desired fiber orientation, however, may be dependent of the requirements of the application.

The bioresorbable glass fiber may be used as continuous form as strands, roving's, yarns, tapes, textiles or chopped to form chopped strand segments. The chopped strand segments may be compounded with a polymeric resin during an extrusion process and the resulting short fiber, compounded pellets. On the other hand, the continuous fiber strand packages may be used in continuous fiber thermoplastic composite fabrication using a long fiber thermoplastic (LFT) process to form continuous glass fiber reinforced polymer strands, rods, tapes, textiles or chopped long fiber reinforced pellets. These forms or structures, in turn, may be used to form hybrid composite articles.

In an example of the hybrid composite, a continuous glass fiber reinforced polymer matrix is used with magnesium or magnesium alloy comprising a bioresorbable polymer matrix and continuous bioresorbable reinforcing glass fiber, wherein the glass fiber has a tensile strength of about or over 2000 MPa. This enables obtaining a hybrid composite tensile strength of more than 450 MPa, and a composite flexural strength of more than 450 MPa. Thereby an orthopedic implant having composite tensile strength of more than 450 MPa, and a composite flexural strength of more than 450 MPa, is obtained.

The term "bioresorbable glass fiber reinforced polymer matrix" refers to any suitable depositable structure comprising the bioresorbable polymer matrix and the bioresorbable reinforcing fiber or fiber bundle in the structure. The bioresorbable reinforcing fiber may be discontinuous or continuous or mixture of those in the structure.

The weight ratio of the continuous bioresorbable reinforcing fiber or fiber bundle to the bioresorbable polymer is preferably such that the bioresorbable reinforcing fiber content is 1 to 99 weight-% of the total weight of the bioresorbable glass fiber reinforced polymer matrix, preferably 20 to 80 wt %, more preferably from 30 to 70 wt % and most preferably 40 to 60 wt %.

The smallest dimension of the bioresorbable glass fiber reinforced polymer matrix is preferably from 0.05 mm to 100 mm, more preferably 0.1 mm to 20 mm, even more preferably from 0.5 mm to 10.0 mm, most preferably from 0.8 mm to 5.0 mm.

The bioresorbable polymer may be a homopolymer or a copolymer, including random copolymer, block copolymer, or graft copolymer. Further, the bioresorbable polymer may be a linear polymer, a branched polymer, or a dendrimer. The bioresorbable polymers may be of natural or synthetic origin.

One or more of the following resorbable polymers, copolymers and terpolymers may be used as suitable bioresorbable polymers. For example, polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/e-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/e-caprolactone terpolymers, PLA/polyethylene oxide copolymers; polydepsipeptides; unsymmetrically 3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone—poly-s-capralactone, Polytyrosines and its copolymers; polyacrylamides, poly(e-caprolactone-DL-lactide) copolymers; methylmethacrylate-N-vinylpyrrolidone copolymers; Polyvinylpyrrolidone and its copolymers; polyesteramides; polyacrylic acids, polybutylene succinate and its copolymers; polyoxazolines, Polyethylene glygols, polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanoic acids; polycarbonates; polyorthoesters; polyphosphates; Polyphosphazenes; poly(ester anhydrides); biodegradable liquid crystal polymers; Xanthan Gum; Pectins; Dextran; Carrageenan; Guar Gum, Cellulose Ethers; Glucomannan; Sodium CMC; HPC; HPMC; and mixtures thereof; and natural polymers, such as sugars; Starch or Starch Based Derivatives, cellulose and cellulose derivatives, polysaccharides, collagen, chitin, chitosan, fibrin, hyaluronic acid, polypeptides and proteins. Mixtures and copolymers of any of the above-mentioned polymers and their various forms may also be used.

Particular examples of suitable bioresorbable polymers include, but are not limited to, polymers made from, obtained from or comprising, lactide, glycolide, caprolactone, valerolactone, carbonates, dioxanones, 6-valerolactone, ethylene glycol, ethylene oxide, esteramides, y-hydroxyvalerate, B-hydroxypropionate, alpha-hydroxyacid, hydroxybuterates, polyorthoesters, hydroxy alkanoates, tyrosine carbonates, polyimide carbonates, polyimino carbonates, polyurethanes, polyanhydrides, and copolymers and any combinations thereof. Suitable natural biodegradable polymers include collagen, chitin, chitosan, cellulose, polyaminoacids, polysaccharides, and copolymers, derivatives and combinations thereof.

The bioresorbable polymer is preferably selected from the group consisting of bioabsorbable polyesters, PLLA (poly-L-lactide), PDLLA (poly-DL-lactide), PLDLA, PGA (polyglycolic acid), PLGA (poly-lactide-glycolic acid), PCL (polycaprolactone), PLLA-PCL and combinations thereof.

In addition to the bioresorbable polymer the bioresorbable glass fiber reinforced polymer matrix comprises a bioresorbable reinforcing glass fiber or fiber bundle.

The average fiber diameter of a single reinforcing fiber may be in the range of 1-100 micrometers, preferably 5-30 micrometers, more preferably 10-20 micrometers. This may be detected and determined microscopically.

In a preferred example, the bioresorbable reinforcing glass fiber or fiber bundle comprises or is comprised of phosphate or silica-based mineral compound. Most preferably the bioresorbable reinforcing fiber or fiber bundle is a melt derived silica-based bioresorbable glass fiber. In one example the bioresorbable glass is selected from silica, phosphate, boron and magnesium based bioresorbable glasses.

Typically, glass fibers are formed by attenuating streams of a molten glass material from a bushing. A sizing composition, or chemical treatment, may comprise lubricants, coupling agents, film-forming, binders, emulsifiers, surfactants, melt viscosity reducers, compatibilizers, adhesion promoters and anti-static agents, wetting agents, dispersing agents, catalysts, but not limited on those. Sizing's are typically applied to the fibers after they are drawn from the bushing. The sizing composition protects the fibers from inter-filament abrasion and promotes compatibility and adhesion between the glass fibers and the matrix in which the glass fibers are to be used. After the fibers are treated with the sizing composition, they may be dried and formed into a continuous fiber strand package or chopped into chopped strand segments. Glass fibers can then be used in the form of continuous or chopped filaments, strands, roving's, woven fabrics, nonwoven fabrics, meshes, and scrims in polymer matrix.

The bioresorbable glass fiber may comprise or have composition in the following wt % ranges (as a percent over the total weight of the glass fiber composition):
$SiO_2$ 40-90 wt %,
$Na_2O$ 1-30 wt %,
$K_2O$ 0-20 wt %,
CaO 5-30 wt %,
MgO 0-20 wt %,
$P_2O_5$ 0-20 wt %,
$B_2O_3$ 0-20 wt %,
$Al_2O_3$ 0-10 wt %,
$CaF_3$ 0-25 wt %,
SrO 0-10 wt %, and
$Li_2O$ 0-5 wt %.

In a first example the bioresorbable glass fiber has composition in the following wt % ranges:
$SiO_2$ 50-75 wt %,
$Na_2O$ 5-20 wt %,
$K_2O$ 0-10 wt %,
CaO 5-25 wt %,
MgO 0-10 wt %,
$P_2O_5$ 0.5-5 wt %,
$B_2O_3$ 0-15 wt %,
$Al_2O_3$ 0-5 wt %, and
SrO 0-5 wt %.

In a second example the melt derived bioabsorbable glass fiber has composition in the following wt % ranges:
$SiO_2$ 60-72 wt %,
$Na_2O$ 10-20 wt %,
$K_2O$ 0.1-10 wt %,
CaO 5-15 wt %,
MgO 1-10 wt %,
$P_2O_5$ 0.5-2 wt %,
SrO 0-3 wt %, and
$B_2O_3$ 0-10 wt %.

In a third example the melt derived bioabsorbable glass fiber has composition in the following wt % ranges:
$SiO_2$ 60-72 wt %,
$Na_2O$ 10-20 wt %,
$K_2O$ 0.1-10 wt %,
CaO 5-15 wt %,
MgO 1-10 wt %,
$P_2O_5$ 0.5-2 wt %,
SrO 0.1-3 wt %, and
$B_2O_3$ 0.1-10 wt %.

The sum of the ingredients of the compositions sums up to 100%.

Therefore, the present application also discloses a bioresorbable glass fiber and a composition for forming the bioresorbable glass fiber. As used herein, the term "bioresorbable glass fiber" is meant to denote that the glass fiber can be dissolved and/or degraded by the action of water or other natural agents. The bioresorbable fibers may be used as reinforcement for composite parts. The bioresorbable reinforcing glass fiber may be bioactive and/or osteoconductive depending on the glass composition The bioresorbable glass fiber may be used in conjunction with bioresorbable polymers and the magnesium alloy to form a hybrid composite product that is naturally non-toxic, biocompatible, bioresorbable, biosoluble and biodegradable over a period of time. The bioresorbable fibers have mechanical properties comparative to conventional, non-soluble glass fibers, have a slow to high rate of dissolution in an aqueous medium i.e. low hydrolytic strength and are easily fiberized.

In an advantageous example of the hybrid composite, the bioresorbable glass fiber reinforced polymer matrix comprises a bioresorbable polymer which is preferably selected from the group consisting of bioresorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof; and the bioresorbable reinforcing glass fiber or fiber bundle comprised of a melt derived bioresorbable glass fiber. Preferably the composition of the melt derived bioresorbable glass fiber is as defined above.

In addition to polymer matrix and the bioresorbable reinforcing glass fiber or fiber bundle the bioresorbable glass fiber reinforced polymer matrix may also comprise a bioresorbable sizing in bioresorbable reinforcing glass fiber for improving adhesion between inorganic glass and organic polymer phase, improve processability of the bioresorbable glass fiber reinforced polymer matrix and fiber dispersion in polymer matrix.

Additionally or alternatively the bioresorbable glass fiber reinforced polymer matrix may also comprise one or more reinforcements or filler materials besides of bioresorbable glass fiber, such as ceramic particles (e.g. tricalcium phosphate particles), antimicrobial agents, bioactive agents, active pharmaceutical ingredients, other reinforcing fibers may be comprise other bioresorbable glass composition or glass-like materials, a ceramic, a mineral composition such as hydroxyapatite, tricalcium phosphate, calcium sulfate or calcium phosphate, a cellulosic material, or any other continuous fiber known in the art to increase the mechanical properties of a bioresorbable polymer. The continuous reinforcing fiber may also be a bioresorbable polymer itself.

One effect of the implants or a structural part is their strength and feasible manufacturing. An implant or structural part thereof can be manufactured by arranging any reinforcing form of magnesium or magnesium alloy and bioresorbable glass fibers in a bioresorbable polymer matrix and using one or more of suitable of polymer or composite processing device(s) or equipment, such as a mechanical processing device, for example an open or closed batch mixer or kneader, extruder including coextrusion and thermoplastic pultrusion, injection molding machine including insert molding, reactive injection molding (RIM), lamination, calenders, transfer molding, compression molding, mechanical machining, pultrusion, solvent casting, 3D printing, filament winding, automated tape lay-up, automated fiber placement or other standard melt processing or melt mixing equipment known in the field and including combinations of aforementioned, producing and/or shaping into an implant or structural part having a desired orientation and ratio of the magnesium or magnesium alloys and continuous bioresorbable glass fibers and/or chopped/cut fibers and/or woven, non-woven mats/textiles.

One effect of the implants according to the present application, both the composite implants and the non-composite implants, is that they disappear from the body by degradation without giving rise to adverse events such as too fast hydrogen evolution.

Depending on the application and purpose of the implant material, the implants, in addition to being biocompatible, also exhibit controlled resorption in the mammalian body. The optimal resorption rate is directly proportional to the renewal rate of the tissue in the desired implantation location. In the case of bone tissue, a considerable proportion of the implant is preferably resorbed/decomposed within 12 to 24 months in the tissue. In cases where more physical support to the healing tissues is desirable, the resorption rate might be several months or even several years. Furthermore, mechanically stable implants having specific structures, such as relatively thin walls, tubes or other parts, for example cannulas, catheters and stents, can be provided.

The implants may be used in medical treatment methods, such as methods comprising inserting the implant into tissue, such as into a subject, for example a patient. The method may be a method for treating a subject in need of therapy for a medical condition, such as a medical condition of a bone and/or cartilage and/or other associated tissues or other body parts. The tissue may be any tissue or a combination of tissues as disclosed herein, such as bone (tissue), or bone (tissue) and soft tissue.

The subject may be human or animal subject. The need of therapy may be caused by a damage in a bone and/or other applicable tissue. For example the subject may suffer from a bone fracture and/or other bone damage, and/or other applicable medical condition, such as from one or more disclosed herein.

For example, such a method may comprise
preferably recognizing a subject in need of treatment or therapy,
providing an implant comprising the implant or part of the implant disclosed herein,
inserting the implant into the subject.

The present application also provides use of the implant for treating a subject with any of the medical treatment methods disclosed herein and/or for treating any of the conditions disclosed herein.

The present application provides a method for preparing or manufacturing a medical device or a part thereof, the method comprising
providing a reinforcing form of magnesium alloy and bioresorbable glass fibers in a bioresorbable polymer matrix in form of or to form composite material,
providing one or more processing device,
processing the composite material with the processing device into a medical device or a part thereof.

The method may comprise first providing magnesium alloy, preferably in a suitable form, providing bioresorbable glass fibers in a bioresorbable polymer matrix, and combining these to form the composite material. A processing device, which may be the same, similar or different as in the subsequent step, may be also used for processing the bioresorbable glass fibers in a bioresorbable polymer matrix.

The formed composite material may be any type of applicable composite material described herein. The process for manufacturing the hybrid composite material may be a continuous process or a batch process.

In order to modify the degradation of the final implants, to enhance their surface properties, or to add biologically active compounds therein, they can be further modified by an additional resorbable polymer coating layer with a process that may include co-extrusion, dip coating, electro spraying, injection molding, solution impregnation or any other known technique used in polymer, pharmaceutical, device or textile industry. The polymers may be those mentioned below.

Hybrid composite serves also as a solution for current problems in the technical field where environmental control and pollution prevention requires sustainable solution with fully degradable material which can be used in structural parts and degraded after life cycle of the product without leaving any harmful and toxic by-products left in the nature.

The following numbered items present some embodiments and combinations thereof.

Further features from the specification may be combined with one or more of the items.

1. An orthopedic implant or a part thereof, comprising biodegradable magnesium alloy, preferably fully biodegradable magnesium alloy, comprising magnesium and
Ca in the range of 0.550-0.700 wt %, and
Zn in the range of 0.400-0.700 wt %,
the biodegradable magnesium alloy consisting of two phases comprising
a first phase comprising magnesium and Zn, and
a second phase less noble than the first phase, the second phase comprising $Mg_2Ca$ precipitates larger than nano-sized.

2. The orthopedic implant or the part thereof of item 1, wherein the biodegradable magnesium alloy comprises Fe 50 ppm or less.

3. The orthopedic implant or the part thereof of any of preceding items, wherein the biodegradable magnesium alloy comprises Fe 20 ppm or less.

4. The orthopedic implant or the part thereof of any of preceding items, wherein the biodegradable magnesium alloy comprises total impurities including Fe in the range of 100-1000 ppm.
5. The orthopedic implant or the part thereof of any of preceding items, wherein the biodegradable magnesium alloy has an average grain size of 40 μm or less.
6. The orthopedic implant or the part thereof of any of preceding items, wherein the biodegradable magnesium alloy has an average grain size, determined as equivalent circular diameter (ECD), of 2-20 μm, wherein at least 10% of grains have a grain size above 5 μm.
7. The orthopedic implant or the part thereof of any of preceding items, wherein the ratio of weight percentages Ca:(Zn-0.2) is 1.1 or more.
8. The orthopedic implant or the part thereof of any of preceding items, wherein the magnesium alloy comprises total impurity of Al, Cu, Fe, Mn, Si, Y, Zr, Cd, Pb, Ni, Co, V, Li, Sb and rare earth elements of 1000 ppm or less.
9. The orthopedic implant or the part thereof of any of preceding items having a tensile strength of 260 MPa or more, a yield strength of 200 MPa or more and/or elongation at break of 10% or more, determined according to ASTM B557M-15.
10. The orthopedic implant or the part thereof of any of preceding items comprising a coating and/or a surface treatment.
11. The orthopedic implant or the part thereof of any of preceding items, in a form of a composite with one or more biodegradable polymer(s), glass fiber(s), bioglass and/or ceramic material(s).
12. The orthopedic implant or the part thereof of any of preceding items, which is a fully biodegradable implant comprising the biodegradable magnesium alloy as a self-supporting core embedded in bioresorbable glass fiber reinforced polymer matrix
13. The orthopedic implant or the part thereof of any of preceding items, comprising or consisting of a plate, a pin, a tack or a nail, a bolt, a clamp, a clip, a mesh, a scaffold, a cage, a stent, or a cervical wedge or a lumbar cage for vertebral fusion and other operations in spinal surgery.
14. The orthopedic implant or the part thereof of any of preceding items, which is selected from a screw, an intramedullary nail, a pin, a Kirschner wire and staple.
15. A method for preparing biodegradable magnesium alloy, the method comprising
providing magnesium alloy comprising
Ca in the range of 0.550-0.700 wt %, and
Zn in the range of 0.400-0.700 wt %,
heating the magnesium alloy to a temperature of more than 250° C., such as 255° C. or more, for example 260° C. or more,
to form the heated magnesium alloy into biodegradable magnesium alloy preferably comprising Fe 50 ppm or less, and having an average grain size of 40 μm or less and consisting of two phases comprising
a first phase comprising magnesium and Zn, and
a second phase less noble than the first phase, the second phase comprising $Mg_2Ca$ precipitates larger than nanosized.
16. The method of item 15, comprising heating the magnesium alloy to a temperature in the range of 260-400° C.

17. A method for preparing the orthopedic implant or the part thereof, of any of items 1-14, the method comprising
providing a biodegradable magnesium alloy object having an average grain size of 40 μm or less and comprising magnesium and
Ca in the range of 0.550-0.700 wt %,
Zn in the range of 0.400-0.700 wt %, and
preferably Fe 50 ppm or less,
the biodegradable magnesium alloy consisting of
a first phase comprising magnesium and Zn, and
a second phase less noble than the first phase, the second phase comprising $Mg_2Ca$ precipitates larger than nanosized, and
forming the biodegradable magnesium alloy object into the orthopedic implant or the part thereof.
18. The method of item 17, comprising
providing biodegradable magnesium alloy comprising
Ca in the range of 0.550-0.700 wt %,
Zn in the range of 0.400-0.700 wt %,
heating the magnesium alloy to a temperature of more than 250° C., such as 255° C. or more, for example 260° C. or more,
to form the heated magnesium alloy into a biodegradable magnesium alloy object consisting of two phases comprising
a first phase comprising magnesium and Zn, and
a second phase less noble than the first phase, the second phase comprising $Mg_2Ca$ precipitates larger than nanosized,
the biodegradable magnesium alloy comprising Fe 50 ppm or less and having an average grain size of 40 μm or less.
19. The method of any of items 17 or 18, wherein the heating and forming the magnesium alloy comprises heating the magnesium alloy to a temperature of 260° C. or more and extrusion forming the heated magnesium alloy into the biodegradable magnesium alloy object.
20. The method of any of items 17-19, wherein the forming the object into the orthopedic implant or the part thereof comprises processing the object with one or more of the following:
mechanical machining,
laser machining,
wroughting,
water jet processing,
additive manufacturing, and
injection molding, liquid metal molding or metal injection molding, to form the orthopedic implant or the part thereof.
21. The method of any of items 17-20, comprising coating and/or surface treating the orthopedic implant or the part thereof.
22. The orthopedic implant or the part thereof of any of items 1-14 obtained with the method of any of items 17-21.
23. Use of the orthopedic implant of any of items 1-14 for treating a subject with any of the medical treatment methods disclosed herein and/or for treating any of the conditions disclosed herein, such as a medical condition of a bone.
24. Use of biodegradable magnesium alloy comprising magnesium and
Ca in the range of 0.550-0.700 wt %,
Zn in the range of 0.400-0.700 wt %, and
preferably Fe 50 ppm or less, such as 20 ppm or less, the biodegradable magnesium alloy consisting of two phases comprising
a first phase comprising magnesium and Zn, and
a second phase less noble than the first phase, the second phase comprising $Mg_2Ca$ precipitates larger than nano-sized, for preparing an orthopedic implant, such as the orthopedic implant of any of items 1-14.

25. A method for treating a subject in need of therapy for any of the conditions disclosed herein, such as a medical condition of a bone, the method comprising providing the orthopedic implant of any of items 1-14, inserting the orthopedic implant into the subject.

EXAMPLES

The present implants comprising magnesium alloy were manufactured by processes including casting, extrusion, machining, and heat treating.

Example 1

The present magnesium alloy was casted according to the following steps:
1. Melting: The first step in casting magnesium alloys was to melt the raw materials in a furnace in temperature between 650° C. and 750° C. The raw materials included magnesium and alloying elements including calcium and zinc in the amounts disclosed in Example 4 (sample A).
2. Degassing: Once the alloy was melted, it was degassed to remove any impurities or gases that may have been trapped in the melt. This was done using a combination of vacuum and inert gas to remove the impurities.
3. Mold preparation: The mold used for casting was prepared by cleaning and coating it with a mold release agent to prevent the molten metal from sticking to the mold.
4. Pouring: The molten magnesium alloy was poured into the prepared mold and left to cool and solidify.
5. Removal: Once the casting had solidified, it was removed from the mold. The casting was cleaned and finished to remove any excess material or surface imperfections.
6. Heat treatment: The casting was heat treated to further improve its mechanical properties.
7. Machining: Finally, the casting was machined to its final shape and size (billet), ready for the extrusion step.

Example 2

The magnesium alloy casting from example 1 was extruded according to the following steps:
1. Billet Preparation: The first step was to prepare the billet, which is the starting material for the extrusion process. The billet was made by melting the magnesium alloy and casting it into a cylindrical shape.
2. Preheating: The billet was then heated to a temperature slightly below the melting point of the magnesium alloy. This preheating step softened the material and made it easier to extrude.
3. Extrusion: The preheated billet was placed in an extrusion press and forced through a die. The die was made of steel and had a cylindrical cross-sectional shape and the used extrusion temperature was between 400° C. and 450° C. The pressure applied to the billet caused it to flow through the die and take on the cylindrical shape of the die opening.
4. Cooling: The extruded profile was then cooled by air or water. This cooling step helped to harden the magnesium alloy and set the shape of the extruded profile.
5. Cutting: Once the extruded profile had cooled, it was cut to the desired length using a saw.
6. Finishing: The final step was to finish the extruded profile/billet by removing any sharp edges or surface defects. This was done using a combination of sanding, grinding, and polishing.

Example 3

The magnesium alloy profile/billet from example 2 was machined according to the following steps:
1. Profile/billet incoming inspection.
2. Machining implants with a CNC using carbide and TiAl-nitride coated tools without any processing aids.
3. The conformity of the manufacturing process was verified by sampling critical dimensions.
4. Implant cleaning with a 100% ethanol
5. Implant drying in a controlled environment.
6. Implant packaging
7. Implant heat treatment, 2 hours in 160° C. to 180° C.
8. Final inspection of the implants Example 4

Table 1 discloses chemical composition of an example of a biodegradable magnesium alloy according to the present invention (a sample from example 3), especially in respect of impurities. The percentages are by weight.

TABLE 1

Chemical Composition of an Mg-alloy

| Component | | Content |
|---|---|---|
| Alloying elements | Mg | Balance |
| | Ca | 0.59 w-% |
| | Zn | 0.54 w-% |
| Impurities | Fe | 12 ppm |
| | Ni | 13 ppm |
| | Cu | 6 ppm |
| | Mn | 9 ppm |
| | Si | 200 ppm |
| Total Impurities | | 580 ppm |

Table 2 discloses the measured mechanical properties of an example of the biodegradable magnesium alloy according to the present invention (a sample from example 3).

TABLE 2

Mechanical Properties of a magnesium alloy

| | |
|---|---|
| Bending strength | 443 MPa |
| Bending yield strength | 331 MPa |
| Shear strength | 139 MPa |
| Tensile strength | 279 MPa |
| Tensile yield strength | 239 MPa |
| Strain | 21% |

Example 5

Figure 5:
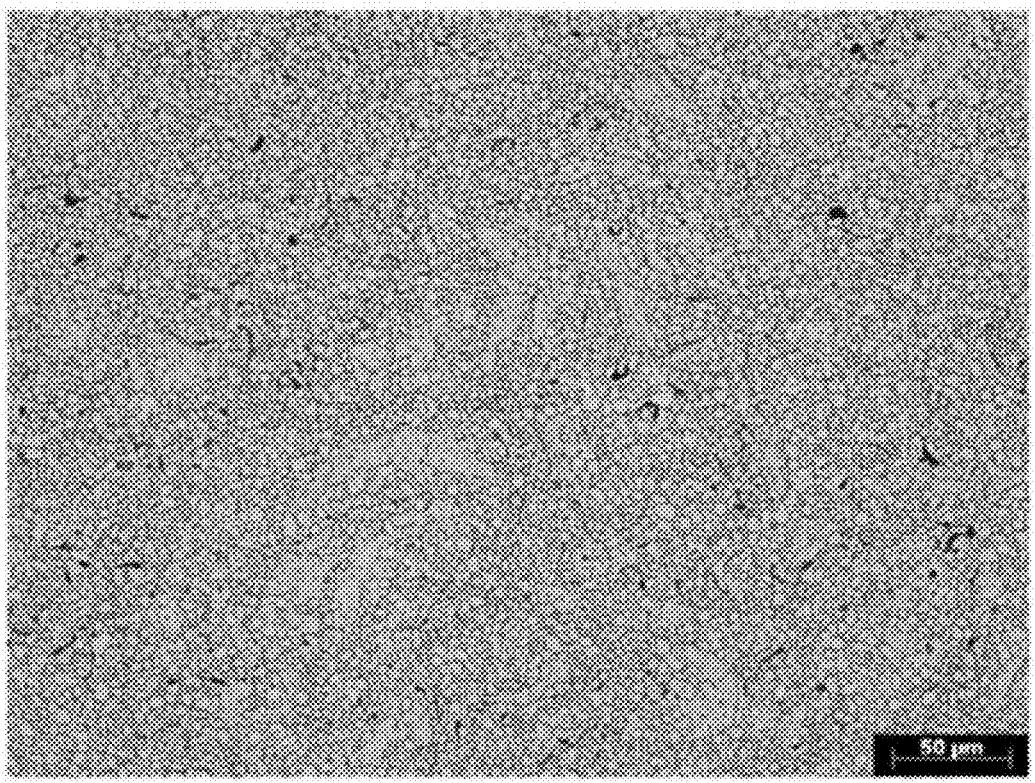
FIG. 5 shows an optical micrograph of etched transverse specimen showing small grain size and precipitations as back spots or areas. Magnification 230×. Scale bar 50 µm. Etchant: solution of ammonium persulfate and water.
Figure 6:
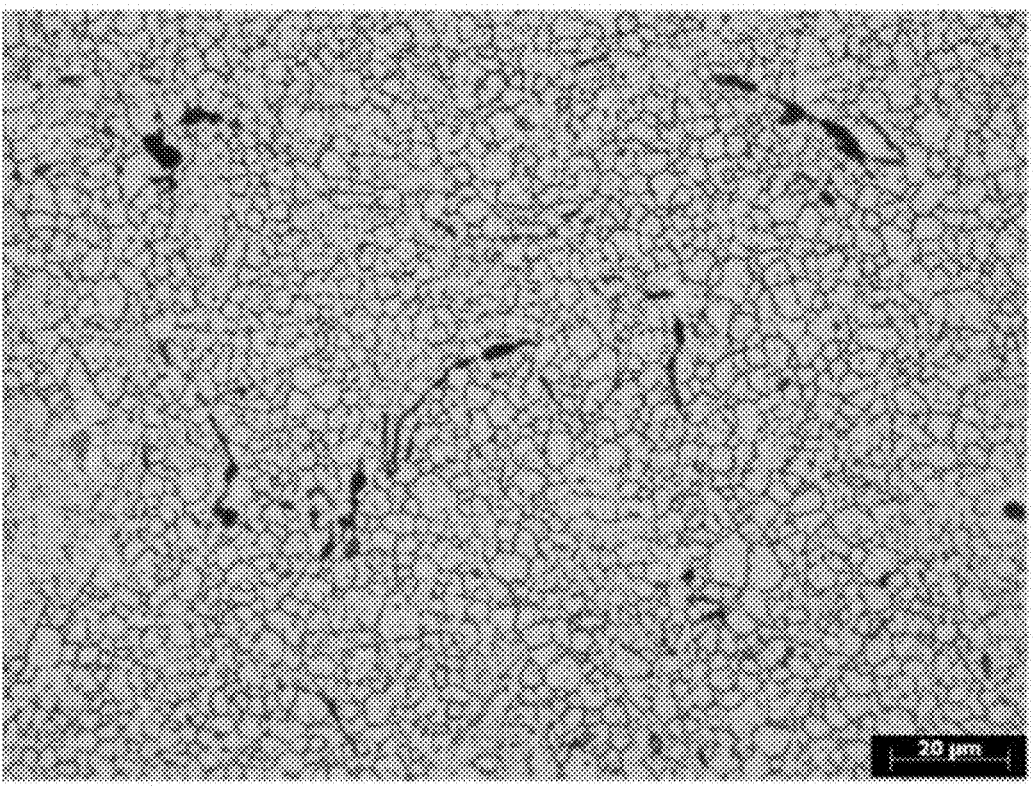
FIG. 6 shows an optical micrograph of etched transverse specimen showing average grain size G13. Magnification 600×. Scale bar 20 µm. Etchant: solution of ammonium persulfate and water.

FIGS. 5 and 6 show optical microscope analyses of present transverse specimen 301 of the biodegradable magnesium alloy according to the present invention (sample from example 3) etched with ammonium persulfate. The small grain size and precipitations as black spots or areas can be seen in FIG. 5. The average grain size G13 can be seen in FIG. 6.

Figure 7A:
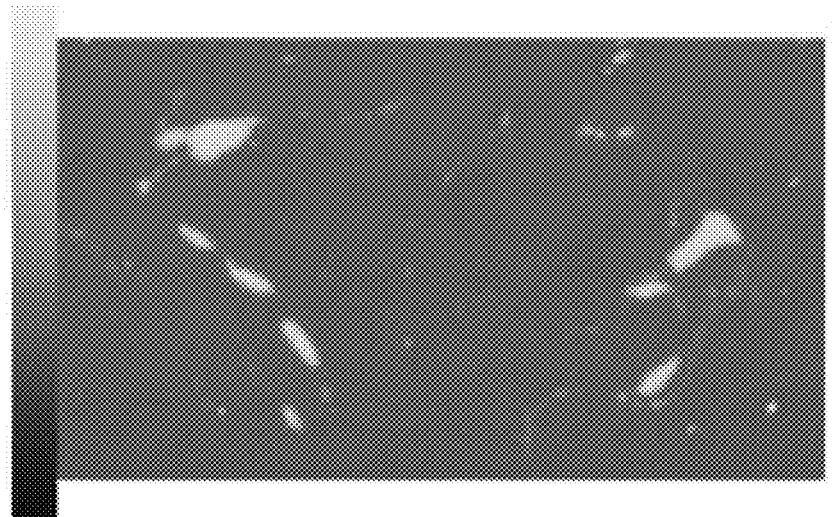
FIGS. 7A-7B show $Mg_2Ca$ precipitates in the present magnesium alloys measured with optical microscopy by University of Tampere. Only $Mg_2Ca$ phase is visible.
Figure 7B:
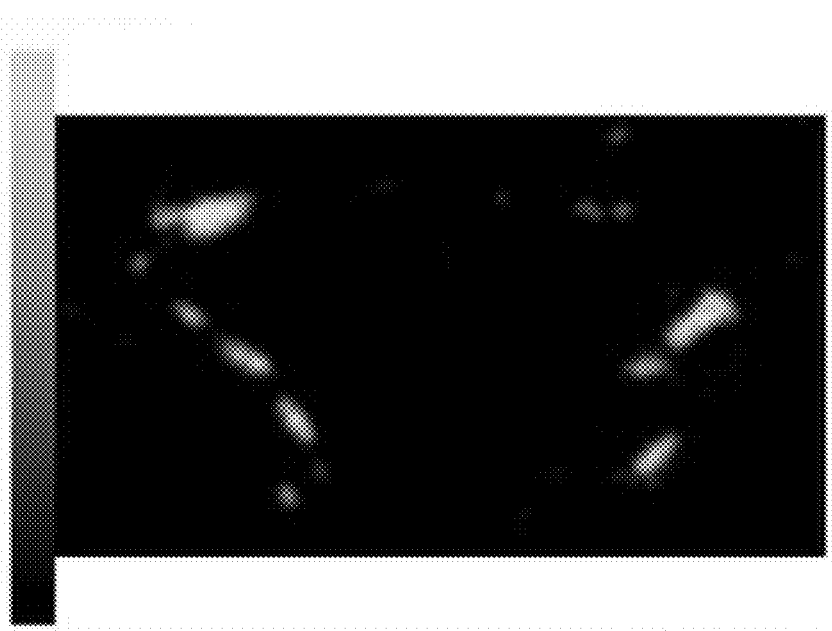

FIG. 7 shows $Mg_2Ca$ precipitates in the present biodegradable magnesium alloys measured by EDX, in backscattering electrons (BSE) mode, measured by SEM EDX. Only $Mg_2Ca$ phase is visible. 7A shows precipitates of the less noble second phase and 7B shows Ca in the precipitates.

Figure 8:
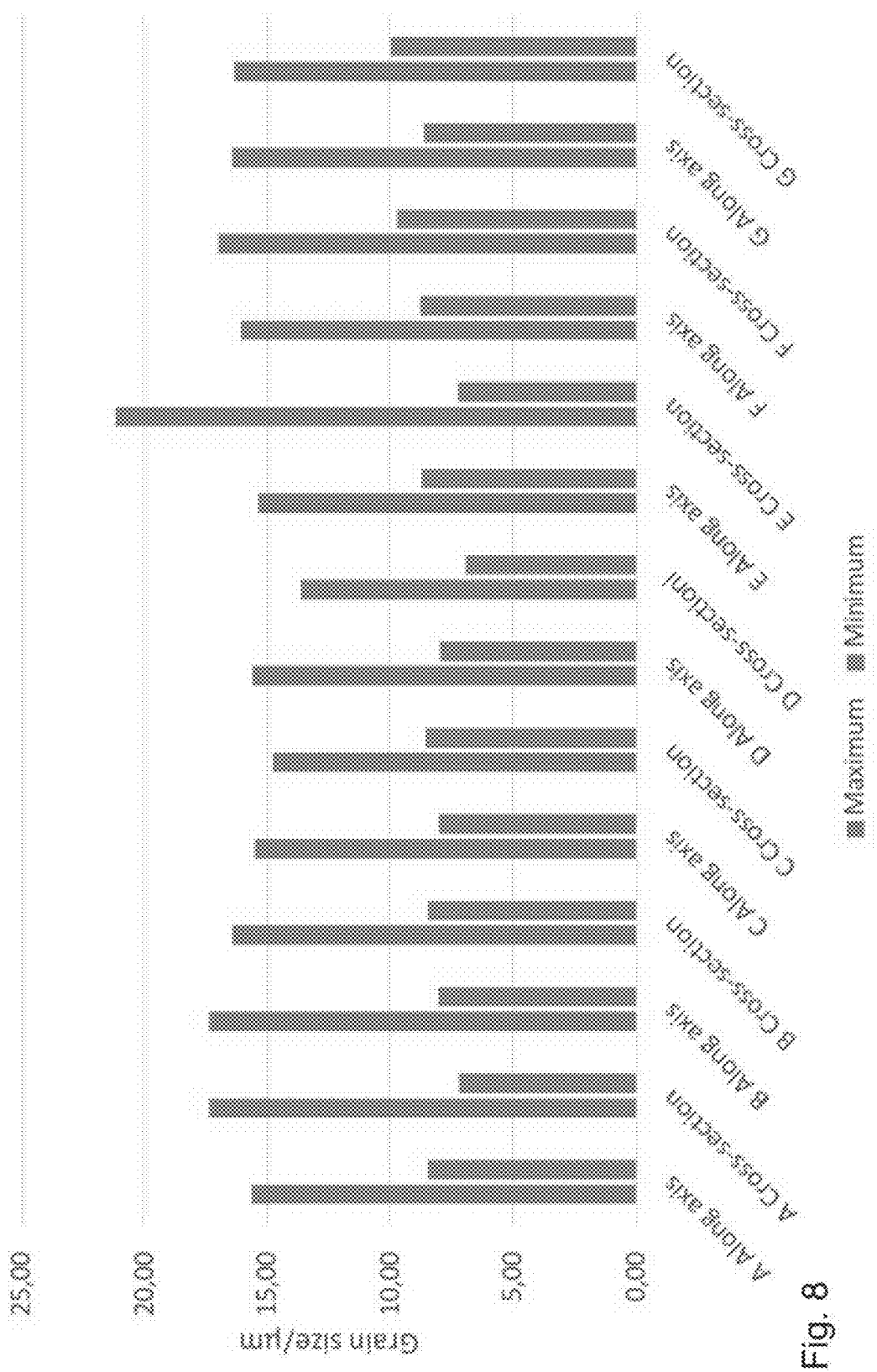
FIG. 8 shows grain size analysis of the present magnesium alloys. Left bars represent maximum sizes and right bars represent minimum sizes.
Figure 9A:
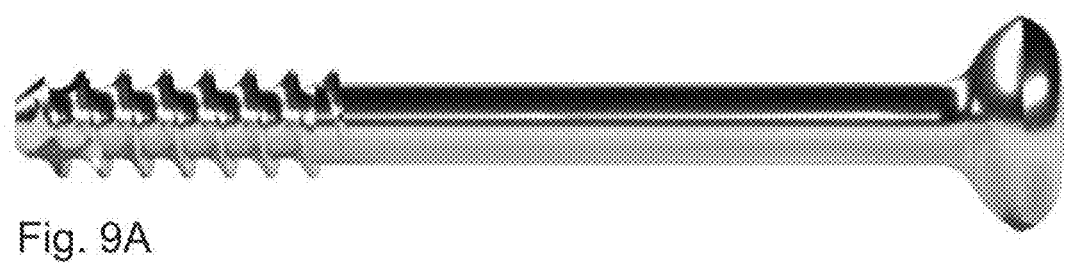
FIG. 9A shows a close view of a surgical screw made from the present magnesium alloy, and FIG. 9B examples of similar surgical screws with different sizes.
Figure 9B:
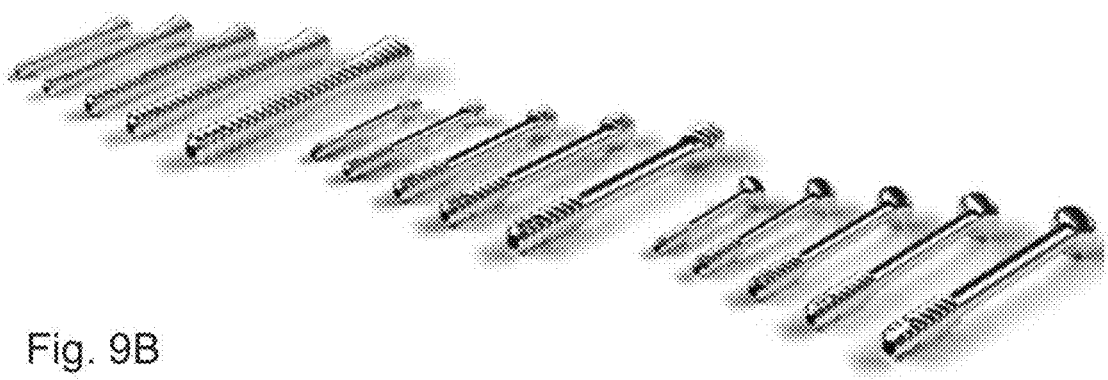

FIG. 8 shows grain size analysis of the present biodegradable magnesium alloys. Left bars represent maximum sizes and right bars represent minimum sizes.

Example 6

Introduction

Pullout strength was used to measure screw fixation strength. The fixation, i.e., pullout force, of the biodegradable magnesium alloy (A) surgical screws prepared from the present magnesium alloy was compared to (B) magnesium alloy with lower calcium content (<0.5%), less impurities (<400 ppm) and smaller grain size (<5 μm) in an in vivo/ex vivo study with a sheep model at multiple time points.

The fixation stability of the screws from both materials has been conducted in the form of in vivo/ex vivo pullout force in mature large animal bone. The screw-bone-interface strength is determined by measuring the force needed to pull the implanted screw out of the bone with an ex vivo axial pullout test at multiple timepoints.

Additionally, in vivo corrosion/resorption rates were determined.

Test Articles

The test articles were surgical screws of 3.5 mm diameter and 16 mm length, which were fully threaded and were made conventional CNC machining. The test articles were sterile.

The test articles made from biodegradable magnesium alloy according to the present invention (A) were heat treated 2 hours in 160° C. Reference articles (B) made from a magnesium alloy with lower calcium content (<0.5%), less impurities (<400 ppm) and smaller grain size (<5 μm) measured as equivalent circular diameter (ECD) were gamma sterilized.

Table 3 discloses differences between material A and B.

TABLE 3

Property differences between the present materials used in the in vivo study A and reference material B

| | | Material | |
|---|---|---|---|
| | | A | B |
| Content | Ca | 0.59% | 0.45% |
| | Zn | 0.54% | 0.45% |
| | Fe | 12 ppm | ~1 ppm |
| | Ni | 13 ppm | ~1 ppm |
| | Cu | 6 ppm | ~1 ppm |
| | Mn | 9 ppm | ~1 ppm |
| | Si | 200 ppm | ~1 ppm |
| | Total Impurities | >400 ppm | <50 ppm |
| Average grain size | [μm] | >5 | 1.67 |

Results

Table 4 discloses the used sample quantities, pullout test results for materials A and B at time zero, 6 weeks, and 12 weeks in ovine tibia.

TABLE 4

In vivo pullout test results for materials A and B

| | | Material | | | | | |
|---|---|---|---|---|---|---|---|
| | | A | | | B | | |
| | | Week | | | | | |
| | | 0 | 6 | 12 | 0 | 6 | 12 |
| | | Number of screws | | | | | |
| | | 10 | 9 | 12 | 7 | 12 | 11 |
| Pullout [N] | Average | 876 | 799 | 821 | 728 | 360 | 509 |
| | St. Dev. | 269 | 335 | 188 | 240 | 190 | 220 |

FIGS. 8A and 8B show surgical screws made from the present magnesium alloy prepared as described in previous.

Example 7

A hybrid composite implant was prepared by using a rigid self-supporting hollow rod machined from the present magnesium alloy as a core, and thermoplastic filament winding this self-supporting core with a filament tape comprising bioresorbable glass fibers and bioresorbable polymer. The obtained hybrid composite article is shown in FIG. 10.

What is claimed is:

1. An orthopedic implant or a part thereof, comprising biodegradable magnesium alloy comprising magnesium and
    Ca in the range of 0.550-0.700 wt %,
    Zn in the range of 0.400-0.700 wt %, and
    Fe 50 ppm or less,
    the biodegradable magnesium alloy consisting of two phases comprising
    a first phase comprising magnesium and Zn, and
    a second phase less noble than the first phase, the second phase comprising $Mg_2Ca$ precipitates larger than nano-sized.

2. The orthopedic implant or the part thereof of claim 1, wherein the biodegradable magnesium alloy comprises Fe 20 ppm or less.

3. The orthopedic implant or the part thereof of claim 1, wherein the biodegradable magnesium alloy comprises total impurities including Fe in the range of 100-1000 ppm.

4. The orthopedic implant or the part thereof of claim 1, wherein the biodegradable magnesium alloy has an average grain size of 40 μm or less.

5. The orthopedic implant or the part thereof of claim 1, wherein the biodegradable magnesium alloy has an average grain size, determined as equivalent circular diameter (ECD), of 2-20 μm, wherein at least 10% of grains have a grain size above 5 μm.

6. The orthopedic implant or the part thereof of claim 1, wherein the ratio of weight percentages Ca:(Zn-0.2) is 1.1 or more.

7. The orthopedic implant or the part thereof of claim 1, wherein the magnesium alloy comprises total impurity of Al, Cu, Fe, Mn, Si, Y, Zr, Cd, Pb, Ni, Co, V, Li, Sb and rare earth elements of 1000 ppm or less.

8. The orthopedic implant or the part thereof of claim 1 having a tensile strength of 260 MPa or more, a yield strength of 200 MPa or more and/or elongation at break of 10% or more, determined according to ASTM B557M-15.

9. The orthopedic implant or the part thereof of claim 1 comprising a coating and/or a surface modification.

10. The orthopedic implant or the part thereof of claim 1, in a form of a composite with one or more biodegradable polymer(s), glass fiber(s), bioglass and/or ceramic material(s).

11. The orthopedic implant or the part thereof of claim 1, which is a fully biodegradable implant comprising the biodegradable magnesium alloy as a self-supporting core embedded in bioresorbable glass fiber reinforced polymer matrix.

12. The orthopedic implant or the part thereof of claim 1, wherein the orthopedic implant is in a form of a plate, a pin, a tack or a nail, a bolt, a clamp, a clip, a mesh, a scaffold, a cage, a stent, or a cervical wedge or a lumbar cage for vertebral fusion and other operations in spinal surgery.

13. The orthopedic implant or the part thereof of claim 1, which is selected from a screw, an intramedullary nail, a pin, a Kirschner wire and staple.

14. A method for preparing the orthopedic implant or the part thereof, of claim 1, the method comprising providing a biodegradable magnesium alloy object having an average grain size of 40 μm or less and comprising magnesium and Ca in the range of 0.550-0.700 wt %, Zn in the range of 0.400-0.700 wt %, and Fe 50 ppm or less, the biodegradable magnesium alloy consisting of a first phase comprising magnesium and Zn, and a second phase less noble than the first phase, the second phase comprising $Mg_2Ca$ precipitates larger than nano-sized, and forming the biodegradable magnesium alloy object into the orthopedic implant or the part thereof.

15. The method of claim 14, comprising
providing biodegradable magnesium alloy comprising
Ca in the range of 0.550-0.700 wt %,
Zn in the range of 0.400-0.700 wt %,
heating the magnesium alloy to a temperature of 260° C. or more,
to form the heated magnesium alloy into a biodegradable magnesium alloy object consisting of two phases comprising
a first phase comprising magnesium and Zn, and
a second phase less noble than the first phase, the second phase comprising $Mg_2Ca$ precipitates larger than nano-sized,
the biodegradable magnesium alloy comprising Fe 50 ppm or less and having an average grain size of 40 μm or less.

16. The method of claim 14, wherein the heating and forming the magnesium alloy comprises heating the magnesium alloy to a temperature of 260° C. or more and extrusion forming the heated magnesium alloy into the biodegradable magnesium alloy object.

17. The method of claim 14, wherein the forming the object into the orthopedic implant or the part thereof comprises processing the object with one or more of the following:
mechanical machining,
laser machining,
wroughting,
water jet processing,
additive manufacturing, and
injection molding, liquid metal molding or metal injection molding,
to form the orthopedic implant or the part thereof.

18. The method of claim 14, comprising coating and/or surface treating the orthopedic implant or the part thereof.

19. A method for treating a subject in need of therapy for a medical condition of a bone, the method comprising
providing the orthopedic implant of claim 1,
inserting the orthopedic implant into the subject.

* * * * *